(12) United States Patent
Li et al.

(10) Patent No.: US 11,402,383 B2
(45) Date of Patent: Aug. 2, 2022

(54) NUCLEIC ACID ENCODING PCSK9 ANTIBODY

(71) Applicant: AD Pharmaceutical Co., Inc., Science City (CN)

(72) Inventors: Baiyong Li, Guangdong (CN); Zhongmin Wang, Guangdong (CN); Yu Xia, Guangdong (CN); Peng Zhang, Guangdong (CN); Wuxian Ren, Guangdong (CN); Jinan Jiao, Guangdong (CN); Yuanyuan Xu, Guangdong (CN); Dongsheng Dai, Guangdong (CN)

(73) Assignee: AD Pharmaceutical Co., Inc., Science City (CN)

( * ) Notice: Subject to any disclaimer, the term of this patent is extended or adjusted under 35 U.S.C. 154(b) by 252 days.

(21) Appl. No.: 16/855,202

(22) Filed: Apr. 22, 2020

(65) Prior Publication Data

US 2020/0319185 A1 Oct. 8, 2020

Related U.S. Application Data

(62) Division of application No. 15/550,211, filed as application No. PCT/CN2016/073492 on Feb. 4, 2016, now Pat. No. 10,670,604.

(30) Foreign Application Priority Data

Feb. 11, 2015 (CN) .......................... 201510075778.3

(51) Int. Cl.
| | | |
|---|---|---|
| *G01N 33/577* | (2006.01) | |
| *C07K 16/40* | (2006.01) | |
| *A61K 39/395* | (2006.01) | |
| *A61K 51/10* | (2006.01) | |
| *A61K 47/68* | (2017.01) | |
| *C07K 16/28* | (2006.01) | |
| *A61K 39/00* | (2006.01) | |

(52) U.S. Cl.
CPC ......... *G01N 33/577* (2013.01); *A61K 39/395* (2013.01); *A61K 47/68* (2017.08); *A61K 51/10* (2013.01); *C07K 16/2896* (2013.01); *C07K 16/40* (2013.01); *A61K 2039/505* (2013.01); *A61K 2039/545* (2013.01); *C07K 2317/24* (2013.01); *C07K 2317/33* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 8,030,457 B2 * | 10/2011 | Jackson | A61P 25/28 530/387.9 |
| 8,080,243 B2 | 12/2011 | Liang et al. | |
| 8,168,762 B2 | 5/2012 | Jackson et al. | |
| 10,670,604 B2 | 6/2020 | Li et al. | |
| 2009/0326202 A1 | 12/2009 | Jackson et al. | |
| 2012/0195910 A1 | 8/2012 | Wu et al. | |
| 2018/0024131 A1 | 1/2018 | Li et al. | |

FOREIGN PATENT DOCUMENTS

| | | |
|---|---|---|
| CN | 101932607 A | 12/2010 |
| CN | 102333542 A | 1/2012 |
| CN | 103261230 A | 8/2013 |

OTHER PUBLICATIONS

Accession: P01857.1, Oct. 16, 2019, 17 pages.
Accession: P0CG05.1 dated Feb. 15, 2017, replaced by P0DOY2 dated Oct. 16, 2019, total 16 pages.
Alfthan et al., "Properties of a single-chain antibody containing different linker peptides," Protein Eng. 8: 725-731 (1995).
Bird et al., "Single-chain antigen-binding proteins," Science (1988) 242:423-426.
Casset, F. et al., "A peptide mimetic of an anti-CD4 monoclonal antibody by rational design," Biochemical and Biophysical Research Communications, 307:198-205 (2003).
Chan et al., "A proptotein convertase subtilisin/kexin type 9 neutalizing antibody reduces serum cholesterol in mice and nonhuman primates", Proc. Natl. Acad. Sci. U.S.A., 106(24):9820-9825 (2009).
Chen et al. "Selection and analysis of an optimized anti-VEGF antibody: crystal structure of an affinity-matured Fab in complex with antigen", J Mol Biol, Nov. 5, 1999; 293(4):865-881.
Choi, et al., "Recombinant chimeric OKT3 scFv IgM antibodiesmediate immune suppression while reducing T cell activation in vitro," Eur. J. Immunol. 31: 94-106 (2001).
Clark, "Antibody Humanization: A case of the 'Emperor's New Clothes'?" Immunol. Today, 21 (8): 397-402 (2000).
De Pascalis, et al., "Grafting of "Abbreviated" Complementarity-Determining Regions Containing Specificity-Determining Residues Essential for Ligand Contact to Engineer a Less Immunogenic Humanized Monoclonal Antibody," The Journal of Immunology, Sep. 15, 2002, 169(6): 3076-3084.
GenBank No. 3H42_H, https://www.ncbi.nlm.nih.gov/protein/229597974, Oct. 10, 2012, 3 pages.

(Continued)

*Primary Examiner* — Sharon X Wen

(74) *Attorney, Agent, or Firm* — Cooley LLP

(57) ABSTRACT

The present invention belongs to the field of immunology and molecular biology, which relates to an anti-PCSK9 antibody, the pharmaceutical composition and method of use thereof. In particular, the present invention relates to the monoclonal antibody, which can bind PCSK9 specifically, block association of PCSK9 with LDLR, upregulate the amount of LDLR on cell surface, heighten the metabolism of LDL cholesterol and/or triglycerides, and prevent/treat cardiovascular diseases caused by hypercholesterolemia.

19 Claims, 13 Drawing Sheets

Specification includes a Sequence Listing.

(56) References Cited

OTHER PUBLICATIONS

Holliger et al., "Diabodies: small bivalent and bispecific antibody fragments," Proc. Natl. Acad. Sci. USA 90: 6444-6448 (1993).
Hu et al. (1996). "Minibody: A novel engineered anti-carcinoembryonic antigen antibody fragment (single-chain Fv-CH3) which exhibits rapid, high-level targeting of xenografts." Cancer Res. 56(13): 3055-3061.
Huston, et al. "Protein engineering of antibody binding sites: recovery of specific activity in an anti-digoxin single-chain Fv analogue produced in *Escherichia coli*." Proc Natl Acad Sci USA. (1988); 85(16): 5879-5883.
Jones et al., "Replacing the complementarity-determining regions in a human antibody with those from a mouse," Nature, 321: 522-525 (1986).
Kipriyanov et al., "Bispecific tandem diabody for tumor therapy with improved antigen binding and pharmacokinetics," J. Mol. Biol. 293: 41-56 (1999).
Kohler et al., "Continuous cultures of fused cells secreting antibody of predefined specificity," Nature, 256: 495-497 (1975).
Lamminmaki et al., "Crystal Structure of a Recombinant Anti-estradiol Fab Fragment in Complex with 17-Estradiol," Journal of Biological Chemistry 276(39):36687-36694 (2001).
Riechmann et al., Reshaping Human Antibodies for Therapy, Nature, 1988, vol. 332, No. 24 , pp. 323-327.
MacCallum, R.M., et al., "Antibody-antigen Interactions: Contact Analysis and Binding Site Topography," J. Mol. Biol., Oct. 11, 1996, vol. 262: 732-745.
NCBI Reference Sequence NP_001106130.1, Jul. 6, 2019, 4 pages.
NCBI Reference Sequence NP_705793.1, dated Dec. 26, 2019, 6 pages.
NCBI Reference Sequence NP_777596.2, dated Dec. 16, 2019, 7 pages.
Ni et al., A PCSK9-binding antibody that structurally mimics the EGF(A) domain of LDL-receptor reduces LDL cholesterol in vivo, Journal of Lipid Research vol. 52, 2011, pp. 78-86.
Padlan et al., "Structure of an antibody-antigen complex: Crystal structure of the HyHEL-10 Fab-lysozyme complex," PNAS 86:5938-5942 (1989).
Poljak R. J et al., ":Production and structure of diabodies.," Structure 2: 1121-1123 (1994).
Presta, "Antibody engineering," Curr. Op. Struct. Biol., 2:593-596 (1992).
Rashid et al., "Proprotein convertase subtilisin kexin type 9 promotes intestinal overproduction of triglyceride-rich apolipoprotein B lipoproteins through both low-density lipoprotein receptor-dependent and -independent mechanisms," Circulation 130(5): 431-41 (2014).
Roovers, et al., "In vitro characterisation of a monovalent and bivalent form of a fully human anti Ep-CAM phage antibody," Cancer Immunol Immunotherapy 50(1):51-59 (2001).
Rudikoff, S. et al., "Single amino acid substitution altering antigen-binding specificity," Proc. Natl. Acad. Sci. USA, 79:1979-1983 (Mar. 1982).
Vajdos, et al. "Comprehensive functional maps of the antigen-binding site of an anti-ErbB2 antibody obtained with shotgun scanning mutagenesis." Journal of Molecular Biology (2002); 320 (2): 415-428.
Wu, H. et al. "Humanization of a Murine monoclonal antibody by simultaneous optimization of framework and CDR residues", Journal of Molecular Biology (1999); 294.1: 151-162.

* cited by examiner

NUCLEIC ACID ENCODING PCSK9 ANTIBODY

CROSS-REFERENCE TO RELATED APPLICATIONS

This application is a divisional of U.S. Ser. No. 15/550,211, filed on Aug. 10, 2017 (now allowed), which is a U.S. National Phase Application, filed under 35 U.S.C. § 371, of International Application No. PCT/CN2016/073492, filed on Feb. 4, 2016, which claims priority to, and the benefit of Chinese Patent Application No. 201510075778.3, filed on Feb. 11, 2015, the contents of each of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Apr. 21, 2020 is named "AKSO-001_02US_SeqList.txt" and is about 5.09 KB in size.

TECHNICAL FIELD

The invention belongs to the field of immunology and molecular biology, which relates to an anti-PCSK9 antibody, the pharmaceutical composition and methods of use. Specifically, the invention relates to an anti-PCSK9 monoclonal antibody.

TECHNICAL BACKGROUND

Proprotein convertase subtilisin/kexin type 9 (PCSK9) is a type of subtilisin protease with pre-protein convertase activity. PCSK9 is mainly expressed in the liver, the small intestine, and the kidney, yet little in the skin and the nervous system. PCSK9, which is secreted from liver to the blood circulation, can decrease the number of low-density lipoprotein (LDL) receptor (LDLR) on the cell surface through binding and endocytosis. Since LDLR can effectively eliminate LDL in the plasma, less LDLR will promote accumulation of LDL. Therefore, reduced LDLR mediated by PCSK9 will result in an increase in LDL cholesterol (LDL-C). PCSK9 also takes part in lipid metabolism of apolipoprotein B. Secretion of PCSK9 could elevate the triglyceride (TG) level in the gut followed by high hypercholesterolemia (Rashid S., et al., Proprotein convertase subtilisin kexin type 9 promotes intestinal overproduction of triglyceride-rich apolipoprotein B lipoproteins through both low-density lipoprotein receptor-dependent and -independent mechanisms. Circulation. 2014 Jul 29; 130(5): 431-41.).

About 29% of patients with hypercholesterolemia are taking statins. However, 8.2% of patients with hypercholesterolemia are intolerant to statins or could not achieve the desired concentration of cholesterol with statins. It was estimated that a total of 390 million patients with hypercholesterolemia live in the top 7 largest pharmaceutical markets, not including china. According to the report "Investigation of nutrition and health status of Chinese Residents" released by the Ministry of Health on Oct 12 in 2004, 18.8% of adults in China have hypertension, a total of 160 million patients in the entire country, 70 million more than in 1991. The number of dyslipidemia patients has reached 160 million as well.

Currently, it is essential to develop novel immunotherapy antibodies, which can specifically bind to PCSK9 and block the association of PCSK9 and LDLR, which in turn will upregulate LDLR expression on the cell surface, enhance metabolism of LDL and cholesterol, and prevent and treat cardiovascular diseases caused by hypercholesterolemia. Furthermore, it is essential to develop highly effective PSCK9 antibody to enhance the metabolism of TG or to reduce TG level, with long term efficacy.

SUMMARY OF THE INVENTION

Through profound research and creative work, the inventors obtained an anti-PCSK9 monoclonal antibody. The inventors surprisingly found that the monoclonal antibody in the present invention can specifically bind to PCSK9, effectively block the association of PCSK9 and LDLR, upregulate the amount of LDLR expressed on cell membrane, promote the metabolism of LDL cholesterol, and decrease the level of TG with a long half-life in particular. Therefore, this antibody can be used to prevent and/or treat cardiovascular diseases caused by hypercholesterolemia.

The following are summaries of the invention:

The present invention relates to a monoclonal antibody or its antigen binding fragments, whose heavy chain CDR regions are selected from the amino acid sequences SEQ ID NO: 5-7;

And/or whose light chain CDR regions are selected from the amino acid sequences SEQ ID NO: 8-10.

Antibody therapeutics, especially monoclonal antibodies (MAB), showed good efficacy in treatment of many diseases. Conventionally, these therapeutic antibodies are obtained from animals immunized with target antigens or through affinity maturation of antibodies with low binding activity. However, these methods take a lot of time and efforts, and quite frequently cannot target specific antigen epitopes.

The variable regions in heavy and light chains of an antibody govern binding activity. Each chain contains three hypervariable regions. Namely, the complementary determining region (CDR) HCDR1, HCDR2 and HCDR3 in heavy (H) chain, and LCDR1, LCDR2 and LCDR3 in light (L) chain, defined by Kabat, et al. (Sequences of Proteins of Immunological Interest, Fifth Edition (1991), volume 1-3, NIH Publication 91-3242, Bethesda Md.).

The inventors creatively designed 6 CDR regions with specific modifications to enhance the binding activity. To accommodate the changes in CDR regions, amino acids in frameworks were also altered to maintain binding activity and to ensure maximum humanness of the sequences.

Amino acid sequences of 3 CDRs in heavy chain variable region:

```
HCDR1:
                              (SEQ ID NO: 5)
GFTFSSYS

HCDR2:
                              (SEQ ID NO: 6)
ISSSSSYI

HCDR3:
                              (SEQ ID NO: 7)
EYDFWSAYYDAFDV
```

Amino acid sequences of 3 CDRs in light chain variable region

```
LCDR1:
                                (SEQ ID NO: 8)
SRNIGGGND

LCDR2:
                                (SEQ ID NO: 9)
GVI

LCDR3:
                                (SEQ ID NO: 10)
QSFDGSLSGSV
```

In certain embodiments, the said monoclonal antibody or its antigen binding fragments contain heavy chain variable region selected from the amino acid sequence SEQ ID NO: 2;

And/or light chain variable region selected from the amino acid sequence SEQ ID NO: 4.

Using known technologies in the field, such as tools from the National Center for Biotechnology Information (NCBI) website, CDRs in heavy chain and light chain variable regions from the described monoclonal antibody were determined to be SEQ ID NO: 5-7 and SEQ ID NO: 8-10, respectively. In the present invention, this monoclonal antibody is named MAB1.

In certain embodiments, the said monoclonal antibody or its antigen binding fragments contain sequences or parts of the sequences selected from Fab, Fab', F(ab')$_2$, Fd, Fv, dAb, CDRs, single chain antibodies (e.g. scFv), humanized antibodies, chimeric antibodies, or bispecific antibodies.

In certain embodiments, the said monoclonal antibody or its antigen binding fragments bind to PCSK9 protein with $EC_{50}$ less than approximately 100 nM, in particular, less than 10 nM, 1 nM, 0.9 nM, 0.8 nM, 0.7 nM, 0.6 nM, 0.5 nM, 0.4 nM, 0.3 nM, 0.2 nM, 0.1 nM or less, detected preferably by a sandwich ELISA.

In certain embodiments, the said monoclonal antibody or its antigen binding fragments bind to PCSK9 protein with KD less than approximately $10^{-5}$ M, in particular, less than approximately $10^{-6}$ M, $10^{-7}$ M, $10^{-8}$ M, $10^{-9}$ M, $10^{10}$ M, or less.

In certain embodiments, the said monoclonal antibody or its antigen binding fragments contain non-CDR regions from species other than mouse, for example, from human.

The present invention relates to isolated nucleotides, which contain a sequence encoding for heavy chain variable region with CDRs from amino acid sequences SEQ ID NO: 5-7; Preferably, heavy chain variable region with amino acid sequence from SEQ ID NO: 2; More preferably, heavy chain variable region with nucleotide sequence from SEQ ID NO: 1.

The present invention relates to isolated nucleotides, containing a sequence encoding for light chain variable region with CDRs from amino acid sequences SEQ ID NO: 8-10; Preferably, light chain variable region with amino acid sequence from SEQ ID NO: 4; More preferably, light chain variable region with nucleotide sequence from SEQ ID NO: 3.

The present invention relates to a vector, which contains any of the isolated nucleotides.

The present invention relates to a host cell, which contains any of the isolated nucleotides, or the vector.

The present invention relates to methods of producing the said monoclonal antibody or its antigen binding fragments by growing host cell lines under suitable conditions, and recovering the monoclonal antibody or its antigen binding fragments from cell culture.

The present invention relates to conjugates, including the said monoclonal antibody or its antigen binding fragments and a conjugating partner as detectable markers. Preferably, conjugating partners are radioactive isotopes, fluorescein, luminescent materials, colorful substances, or enzymes.

The present invention relates to reagent kits, consisting of the said monoclonal antibody or its antigen binding fragments, or the conjugates claimed in the invention.

Preferably, the reagent kits may contain a secondary antibody, which specifically recognizes the said monoclonal antibody or its antigen binding fragments; optionally, such secondary antibody may contain detectable markers such as radioactive isotopes, fluorescein, luminescent materials, colorful substances, or enzymes.

The present invention relates to preparation of reagent kits consisting of the said monoclonal antibody or its antigen binding fragments, or the conjugates claimed in the invention used in detection of the existence or the level of PCSK9 in samples.

The present invention relates to a pharmaceutical composition comprising the said monoclonal antibody or its antigen binding fragments, or the conjugates claimed in the invention. Optionally, it may also comprise a pharmaceutically acceptable carrier or excipient.

The present invention relates to methods of producing drugs with the said monoclonal antibody or its antigen binding fragments or the conjugates claimed in the invention, in prevention and/or treatment of hypertension, high cholesterol, hypercholesterolemia or cardiovascular diseases caused by these conditions.

The present invention relates to methods of producing drugs with the said monoclonal antibody or its antigen binding fragments, or the conjugates claimed in the invention, with the following purposes:
 a) Bind with PCSK9 specifically,
 b) Block association of PCSK9 with LDLR,
 c) Upregulate the amount of LDLR on cell surface or the level of LDLR in blood plasma,
 d) Lower the level of LDL or LDL-C in blood plasma,
 e) Limit the accumulation of LDL in blood plasma,
 f) Inhibit PCSK9-mediated degradation of the LDLR, or
 g) Heighten the metabolism of LDL cholesterol and/or triglycerides.

The inventors demonstrated that the anti-PCSK9 monoclonal antibody in the present invention can effectively reduce the levels of plasma LDL and/or LDL-C in mice and monkeys, even longer (maintained the reduction of plasma LDL-C in mouse for up to 32 days) than the effects of Evolocumab. Unexpectedly, the anti-PCSK9 monoclonal antibody in the present invention can reduce serum TG level in monkeys for up to 13 days after injection, signifying a good treatment potential. At present, no other anti-PCSK9 antibody has displayed this outcome.

The present invention relates to an in vivo or in vitro method of applying effective doses of the said monoclonal antibody or its antigen binding fragments or the conjugates claimed in the invention for the following purposes:
 a) Bind with PCSK9 specifically,
 b) Block association of PCSK9 with LDLR,
 c) Upregulate the amount of LDLR on cell surface or the level of LDLR in blood plasma,
 d) Lower the level of LDL or LDL-C in blood plasma,
 e) Limit the accumulation of LDL in blood plasma,
 f) Inhibit PCSK9-mediated degradation of the LDLR, or g) Heighten the metabolism of LDL cholesterol and/or triglycerides.

The present invention relates to a method of applying effective doses of the said monoclonal antibody or its antigen binding fragments, or the conjugates claimed in the invention, in prevention and/or treatment of hypertension, high cholesterol, hypercholesterolemia and cardiovascular diseases caused by these conditions.

In certain embodiments, the present invention relates to the said monoclonal antibody or its antigen binding fragments, or the conjugates claimed in the present invention, in prevention and/or treatment of hypertension, high cholesterol, hypercholesterolemia and cardiovascular diseases caused by these conditions.

In certain embodiments, the present invention relates to the applications of the said monoclonal antibody or its antigen binding fragments, or the conjugates claimed in the present invention for the following purposes:
 a) Bind with PCSK9 specifically,
 b) Block association of PCSK9 with LDLR,
 c) Upregulate the amount of LDLR on cell surface or the level of LDLR in blood plasma,
 d) Lower the level of LDL or LDL-C in blood plasma,
 e) Limit the accumulation of LDL in blood plasma,
 f) Inhibit PCSK9-mediated degradation of the LDLR, or
 g) Heighten the metabolism of LDL cholesterol and/or triglycerides.

Definitions

Unless otherwise defined herein, scientific and technical terms used in connection with the present invention shall have the meanings that are commonly understood by those of ordinary skill in the art. Furthermore, laboratory techniques of cell and tissue culture, molecular genetics, oligo- or polynucleotide chemistry, and immunology described herein are those well-known and commonly used in the art. Meanwhile, to better understand the present invention, the following terms, unless otherwise indicated, shall be understood to have the following meanings:

As used in this invention, the term "Amino acid sequence of PCSK9 (Proprotein convertase subtilisin/kexin type 9)" refers to not only the full-length of PCSK9 protein (e.g., human NP_777596.21, mouse NP_705793.1 or monkey NP_001106130.1), but also their fusion fragments, in particular, with Fc of mouse or human IgG (mFc or hFc). Furthermore, understood by those of ordinary skill in the art, the amino acid sequence of PCSK9 protein can have naturally or artificial mutations (including but not limited to substitutions, deletions, and/or additions), not affecting its biological functions.

As used in this invention, the term "$EC_{50}$" refers to the concentration for 50% of maximal effect.

As used in this invention, the term "antibody" refers to immunoglobulin proteins, typically composed of two pairs of polypeptide chains (each pair has a "light" (L) chain and a "heavy" (H) chain). The light chains are classified as κ and λ light chains. The heavy chains are classified as μ, δ, γ, α, or ε, and respectively, define isotype antibodies as IgM, IgD, IgG, IgA and IgE. In light chains and heavy chains, variable regions and constant regions are connected by a "J" region consisting of about 12 or more amino acids. The heavy chain also contains a "D" region with about 3 or more amino acids. Each heavy chain contains a variable region ($V_H$) and a constant region ($C_H$), which consists of 3 domains ($C_H1$, $C_H2$, and $C_H3$). Each light chain contains a variable region ($V_L$) and a constant region ($C_L$), which consists of one domain $C_L$. The constant region can mediate the binding of immune globulin to host tissues or factors, including various cells in the immune system (e.g., effector cells) and the first component (C1q) of the classical complement system. $V_H$ and $V_L$ can also be subdivided into regions with high variability (called complementarity determining region (CDR)), which are separated by relatively conservative regions called framework regions (FR). From the amino terminus to the carboxyl terminus, each $V_H$ and $V_L$ is composed of 3 CDRs and 4 FRs, in the order of FR1, CDR1, FR2, CDR2, FR3, CDR3, and FR4. The variable regions ($V_H$ and $V_L$) of the heavy chain and light chain form the antibody binding site. Distribution of amino acids to the regions or domains follows the definitions by Kabat in Sequences of Proteins of Immunological Interest (National Institutes of Health Bethesda, Md. (1987 and 1991)), or Chothia & Lesk (1987) Mol. Biol., 196:901-917; or Chothia et al. (1989) Nature, 342:878-883. The term "antibody" is not restricted by any particular method of producing them. For example, it includes, in particular, recombinant antibodies, monoclonal antibodies, and polyclonal antibodies. Antibodies can be different isotypes, for example, IgG (such as IgG1, IgG2, IgG3, or IgG4 subtype), IgA1, IgA2, IgD, IgE, or IgM antibodies.

As used in this invention, the term "antigen binding fragments" refers to a polypeptide containing fragments of a full-length antibody, maintaining the ability to bind specifically to the same antigen, and/or to compete with the full length antibody against the antigen, which is also called "the antigen binding portion". See Fundamental Immunology, Ch. 7 (Paul, W., ed. 2, Raven Press, N. Y. (1989)), including the entire article and references in this invention for all purposes. Antigen binding fragments can be generated by recombinant DNA techniques or by cleaving intact antibodies with proteolytic enzymes or chemicals. In some cases, the antigen binding fragments include Fab, Fab', F(ab')$_2$, Fd, Fv, dAb, and CDR fragments, single chain antibodies (e.g., scFv), chimeric antibodies, and diabody, including at least a portion of the antibody which is sufficient to confer a specific antigen binding capacity.

As used in this invention, the term "Fd fragment" refers to an antibody fragment composed of $V_H$ and $C_H1$ domains; the term "Fv fragment" refers to an antibody fragment composed of $V_L$ and $V_H$ domains; the term "dAb fragment" refers to an antibody fragment composed of $V_H$ domain (Ward et al., Nature 341: 544-546 (1989)); the term "Fab fragment" refers to an antibody fragment composed of $V_L$, $V_H$, $C_L$, and $C_H1$ domains; the term "F(ab')$_2$ fragment" refers to an antibody fragment composed of two Fab fragments connected through the disulfide bridge in the hinge region.

In some cases, the antigen binding fragment is a single chain antibody (scFv, for example), a single polypeptide chain composed of $V_L$ and $V_H$ domains linked together, (see, for example, Bird et al., Science 242: 423-426 (1988) and Huston et al., Proc. Natl. Acad. Sci. USA 85: 5879-5883 (1988)). Such scFv molecules may have a general structure: $NH_2$—$V_L$-linker-$V_H$—COOH or $NH_2$—$V_H$-linker-$V_L$—COOH. The appropriate linker may be a repeat of GGGGS or its variants. For example, amino acid sequence (GGGGS)$_4$ or its variants can be used (Holliger et al., (1993), Proc. Natl. Acad. Sci. USA 90: 6444-6448). Other linkers had been described by Alfthan, et al., (1995), Protein Eng. 8: 725-731, Choi, et al., (2001) Eur. J. Immunol. 31: 94-106, Hu, et al., (1996), Cancer Res. 56: 3055-3061, Kipriyanov et al., (1999), J. Mol. Biol. 293: 41-56 and Roovers, et al., (2001) Cancer Immunol.

In some cases, the antigen binding fragment is a diabody, namely, a dimeric antibody fragment, whose $V_H$ and $V_L$ domains are expressed on a single polypeptide chain. However, a very short linker does not allow pairing between the two domains of the same chain, forcing the domain to pair with a complementary domain on another chain to generate two antigen binding sites (see, for example, Holliger P. et al., Proc. Natl. Acad. Sci. USA 90: 6444-6448 (1993), and Poljak R. J. et al., Structure 2: 1121-1123 (1994)).

Using conventional techniques known by those of ordinary skill in the art (such as recombinant DNA technology or enzymatic/chemical cleavage), the antigen binding fragment (such as the above antibody fragments) may be obtained from a given antibody, and screened for specificity in the same manner as for the full antibody.

In this invention, unless specified otherwise, the term "antibody" refers to not only the intact antibody, but also the antigen binding fragments of the antibody.

As used in this invention, the terms "mAb" and "monoclonal antibodies" refers to an antibody or a fragment of an antibody that is derived from a group of highly homologous antibodies, i.e. from a group of identical antibody molecules, except for mutations that may arise spontaneously. Monoclonal antibody has high specificity against a single epitope on the antigen. Polyclonal antibodies are different from monoclonal antibodies, containing at least 2 or more different antibodies, which usually recognize different epitopes on the antigen. Monoclonal antibodies can be obtained with hybridoma technology reported originally by Kohler et al., (Nature, 256: 495, (1975)), as well as recombinant DNA Technology (see U.S. Pat. No. 4,816,567).

As used in this invention, the term "humanized antibody" refers to an antibody or its fragments, derived from a human immunoglobulin (receptor antibody), whose CDRs or part of CDRs are replaced by the CDR regions of a non-human antibody (donor antibody), where the donor antibody may be a non-human antibody (for example, mice, rats, or rabbits) with predictive specificity, binding affinity, or reactivity. In addition, some amino acid residues of the receptor antibody framework region (FR) can also be replaced by the corresponding amino acid residues of the non-human source, or replaced by the amino acid residues of other antibodies to further improve or optimize the performance of the antibody. For more details on humanized antibodies, see for example Jones, et al., Nature, 321: 522-525 (1986); Reichmann et al., Nature, 332: 323-329 (1988); Presta, Curr. Op. Struct. Biol., 2: 593-596 (1992); and Clark, Immunol. Today, 21: 397-402 (2000).

As used in this invention, the term "Epitope" refers to a site on the antigen that the immunoglobulin or antibody can specifically bind to. "Epitope" is also known as the "antigenic determinant" in this field. Epitope or antigenic determinants usually consist of chemically active surface groupings of molecules, such as amino acids or sugar side chains, and usually have specific three dimensional structural characteristics, as well as specific charge characteristics. For example, epitope is usually a unique spatial conformation including at least 3, 4, 5, 6, 7, 8, 9, 10, 11, 12, 13, 14, or 15 consecutive or non-consecutive amino acids, which may be "linear" or "conformational". See, for example, Epitope Mapping Protocols in Methods in Molecular Biology, volume 66, G. E. Morris, Ed. (1996). In a linear epitope, the interacting points between the protein and interacting molecule (e.g., antibodies) exist linearly along the first order of amino acids of the protein, where in a conformational epitope, the interacting points are amino acid residues that are separated from each other along the first order of amino acids of the protein.

As used in this invention, the term "isolate" or "isolated" means obtained by artificial means in the natural state. If there is a certain kind of "isolated" matter or component in nature, it may be due to the change in its natural environment, or isolated from the natural environment, or both. For example, polynucleotide or polypeptide in a natural existence in a living animal will be called "isolated" if it was separated with high purity in the same natural state. The term "isolate" or "isolated" does not exclude existence of artificial or synthetic material, or other impurities that does not affect the activity.

As used in this invention, the term "E. coli expression system" refers to the expression system composed of Escherichia coli (strain) and vector, where E. coli (strain) is commercially available, including but not limited to: GI698, ER2566, BL21 (DE3), B834 (DE3), and BLR (DE3).

As used in this invention, the term "vector" refers to a nucleic acid delivery vehicle that can be inserted with a polynucleotide. The vector that can express protein when inserted with a polynucleotide is called an expression vector. Vectors can be inserted into the host cell by transformation, transduction, or transfection, so that the carried genetic substances can be expressed in the host cell. Vectors are well known to the technical personnel in the field, including but not limited to: plasmid; phasmid; cosmid; artificial chromosome such as yeast artificial chromosome (YAC), bacterial artificial chromosome (BAC), or P1 derived artificial chromosome (PAC); phage such as X. phage or M13 phage and animal viruses etc. Animal viruses may include but not limited to, reverse transcriptase virus (including lentivirus), adenovirus, adeno-associated virus, herpes virus (e. g. herpes simplex virus), chicken pox virus, baculovirus, papilloma virus, and papova virus (such as SV40). A vector can contain multiple components that control expression, including but not limited to, promoter, transcription initiation factor, enhancer, selection element, and reporter gene. In addition, the vector may also contain replication initiation site.

As used in this invention, the term "host cell" refers to cells that can import vectors, including but not limited to, prokaryotic cells such as E. coli and Bacillus subtilis, fungal cells such as yeast and Aspergillus, insect cells such as S2 drosophila cells and Sf9, or animal cells such as fibroblast cells, CHO cells, COS cells, NSO cells, HeLa cells, BHK cells, HEK293 cells or human cells.

As used in this invention, the term "specific binding" refers to a non-random binding between two molecules, such as the interaction between the antibody and its target antigen. In some embodiments, a specific binding of an antibody to an antigen means an affinity ($K_D$), for example less than about $10^{-5}$ M, in particular, less than $10^{-6}$ M, $10^{-7}$ M, $10^{-8}$ M, $10^{-9}$ M, $10^{-10}$ M, or less.

As used in this invention, the term "$K_D$" refers to the dissociation equilibrium constant for specific antibody antigen interaction, to describe the binding affinity between antibodies and antigens. The smaller the equilibrium dissociation constant, the tighter the antibody binds antigen, the higher the affinity between the antibody and the antigen. Typically, antibodies bind antigens with a dissociation equilibrium constant less than about $10^{-5}$ M, in particular, less than $10^{-6}$M, $10^{-7}$M, $10^{-8}$M, $10^{-9}$M, $10^{-10}$ M or less, as measured with a BIACORE by surface plasmon resonance (SPR).

As used in this invention, the terms "monoclonal antibodies" and "mAb" have the same meaning and are used interchangeably; the terms "polyclonal antibody" and "PcAb" have the same meaning and are used interchangeably; the terms "polypeptide" and "protein" have the same meaning and are used interchangeably. Also in the present invention, amino acids are usually represented by single letter or three letter abbreviations known to this field. For example, Alanine can be represented as A or Ala.

As used in this invention, the term "effective dose" is defined as an amount of a therapeutic sufficient to partially or completely prevent, or arrest a disease or disorder in a patient. For example, effective prevention dose is the amount to prevent, stop, or delay diseases; effective treatment dose is the amount to cure, or at least partially stop, the disease and its complications in sick patients. Determination of such an effective dose is entirely within the scope of the capabilities of the technical personnel in the field. For example, the effective treatment dose will depend on the severity of the disease, the overall state of the patient's own immune system, the general background of patients such as age, weight and sex, administration of drugs, and other treatments at the same time.

Effects of the Invention

The monoclonal antibody of the present invention (e.g., MAB1) can bind PCSK9 specifically, effectively block the association of PCSK9 to LDLR, upregulate the amount of LDLR expressed on cell surface, promote the metabolism of LDL and cholesterol, reduce the level of TG, and prevent and/or treat cardiovascular diseases caused by hypercholesterolemia with an extended in vivo efficacy.

DETAILED DESCRIPTION OF THE INVENTION

Figure 1:
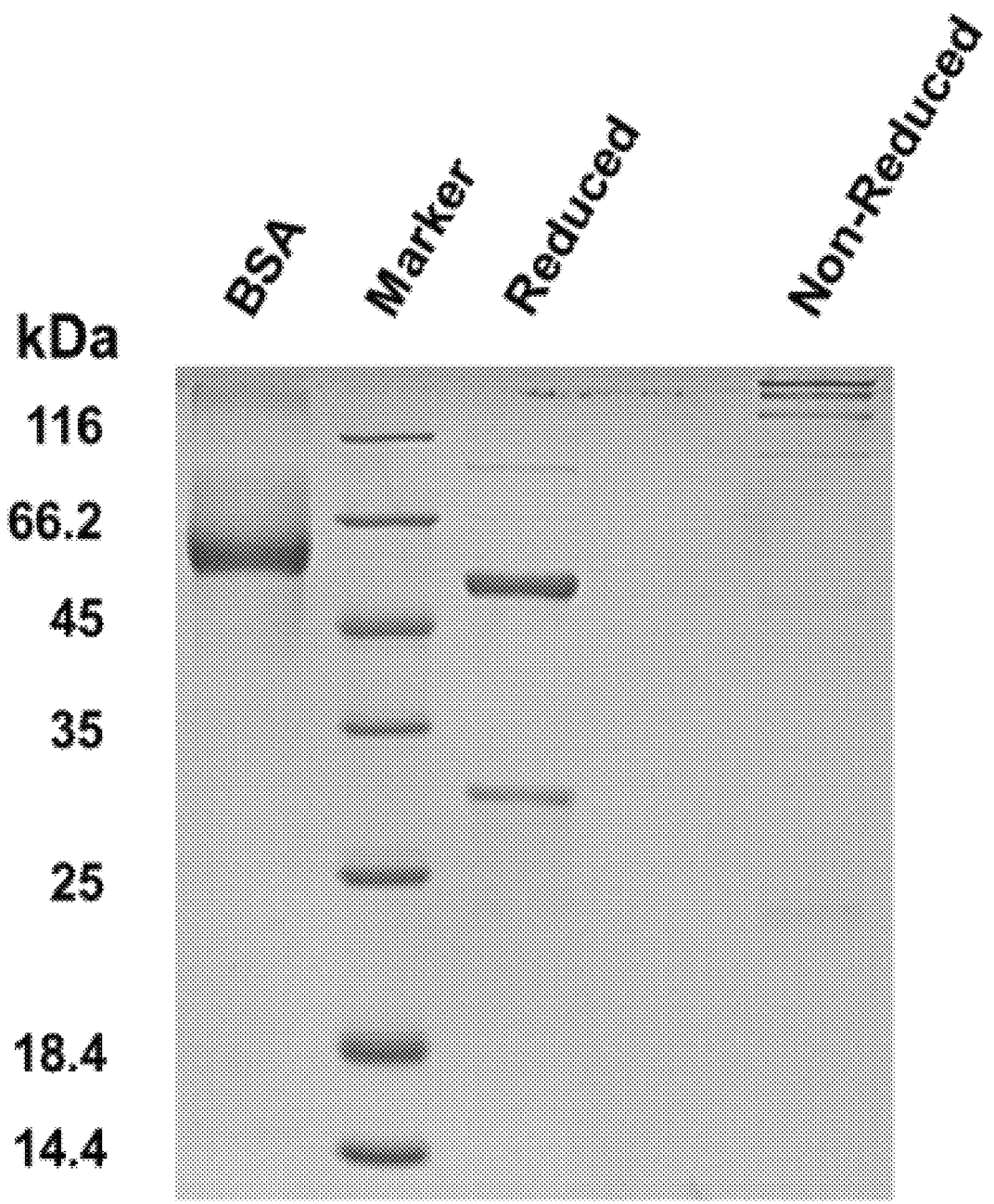
FIG. 1: SDS-PAGE results of anti-PCSK9 antibody. From left to right: 1 µg BSA; 10 µL, marker; 1 µg sample in reduced loading buffer; 1 µg anti-PCSK9 antibody in non-reduced loading buffer.

The invention will now be described in detail. As will be appreciated by one skilled in the art, the following examples are only used for the description of the invention, and not to be deemed to limit the scope of the invention. The cases without the specific descriptions of techniques or conditions were carried out in accordance with the literature in the field (e.g., Guide to Molecular Cloning, written by J Sambrook, et al, translated by Peitang Huang, et al, third Edition, Science Press) or in accordance with the product instruction manual. The reagents or instruments with no specified manufacturer were all conventional products available commercially.

In the examples of the present invention, the mice were purchased from the Guangdong Medical Laboratory Animal Center.

The positive control antibody of the present invention is Evolocumab of Amgen (Joyce C. Y. A proprotein convertase subtilisin/kexin type 9 neutralizing antibody reduces serum cholesterol in mice and nonhuman primates. Proc. Natl. Acad. Sci. USA, 2009, 106(24):9820-5).

Example 1: Preparation of Human, Mouse, and Monkey PCSK9-TEV-his6 Fusion Proteins 1. Gene Synthesis of PCSK9-TEV-his6

The amino acid sequences of human (NCBI Reference Sequence: NP_777596.21), mouse (NCBI Reference Sequence: NP_705793.1) and monkey (NCBI Reference Sequence: NP_001106130.1) PSCK9 were combined with that of TEV-his6.

The corresponding nucleotide sequences of human, mouse, and monkey fusion proteins were optimized and synthesized by GenScript Inc. respectively.

2. The Plasmids of pUC57Simple-PCSK9-TEV-his6

The synthesized PCSK9-TEV-his6 genes were cloned into pUC57simple vector (Provided by GenScript, Inc.) to obtain pUC57simple-PCSK9-TEV-his6 plasmids.

Construction of recombinant plasmids of pcDNA3-PCSK9-TEV-his6: plasmids pUC57simple-PCSK9-TEV-his6 were digested by XbaI and BamHI. Recovered gene fragments of PCSK9-TEV-his6 from gel electrophoresis were ligated with pcDNA3.1 expression vector (Purchased from Invitrogen) to obtain pcDNA3.1-PCSK9-TEV-his6 plasmids, which were transfected into competent *E. coli* cells DH5a (purchased from TIANGEN Biotech Co.) for plating following the instruction manual. The positive clones were selected and scaled up for purifying large quantities ofpcDNA3.1-PCSK9-TEV-his6 DNA using a reagent kit according to the manufacturer's instructions.

3. Expression, Purification of PCSK9-TEV-his6 and Peparation of PCSK9 Atigens 7 days after transfecting recombinant plasmids of human, mouse and monkey pcDNA3.1-PCSK9-TEV-his6 into 293F cells, the culture media were processed by high-speed centrifugation and filtration using microporous membrane, and then purified by HisTrap column (ÄKTA Purifier 10, GE) according to the instruction manual provided by the manufacturer to obtain the human, mouse and monkey fusion proteins. The fusion proteins were digested using TEV proteinase and purified further by Ni-NTA column to obtain PCSK9 antigens.

Example 2: Expression and Purification of LDLR Protein

1. Construction of hLDLR-His Plasmid

The hLDLR-His gene fragment was amplified by PCR with LDLR human cDNA (purchased from Origene, Inc.) as a template and purified with common a DNA purification kit and gel electrophoresis. The recovered gene fragment hLDLR-His was digested by XbaI and HindIII-HF and cloned into pcDNA3.1 expression vector (Purchased from Invitrogen) by T4 ligase to obtain pcDNA3.1-hLDLR-his6, which was transfected into competent *E. coli* cells DH5α (purchased from TIANGEN Biotech Co.) for seeding on the Amp+ager plate. The positive clones were identified by PCR and cultured in LB liquid media. The media were submitted to Invitrogen for sequencing and verified by BLAST for containing the correct insert.

2. Expression and Purification of LDLR Protein

The recombinant plasmid pcDNA3.1-hLDLR-his6 was transfected into 293F cells (Invitrogen) using Lipofectamin transfection kit. 7 days after transfection, the culture medium was processed by high-speed centrifugation, concentration, and buffer exchanged into Binding Buffer A, and applied onto HisTrap column (ÄKTA Purifier 10, GE). The protein was eluted with a linear gradient of Elution Buffer A. The purified protein was buffer exchanged using Hitrap Desalting column to Binding Buffer B and loaded to Hitrap Q column. The target protein was eluted with a linear gradient of Elution Buffer B and buffer exchanged to PBS. The final protein was examined by SDS-PAGE in reduced loading buffer.

Example 3: Design, Expression, and Purification of MAB1

1. Antibody Design

To prepare monoclonal antibody MAB1, the inventors creatively designed a series of antibody sequences according to the amino acid sequences and 3-D crystal structure of PCSK9 protein. Through numerous screenings and examinations, MAB1 that binds PSCK9 specifically was finally obtained. The encoding nucleotide and amino acid sequences of heavy chain variable region and light chain variable region of MAB1 were defined in SEQ ID NO: 1-4.

The nucleotide sequence of heavy chain variable region of MAB1 (369bp):

(SEQ ID NO: 1)
GAGGTGCAGCTGGTGGAGTCTGGAGGAGGCCTGGTGCAGCCCGGAAGA

TCTCTGAGACTGAGTTGCGCCGCTTCAGGATTCACCTTTAGCTCCTAC

AGCATGAACTGGGTGCGGCAGGCTCCTGGCAAGGGGCTGGAGTGGGTC

TCCGGAATCTCTAGTTCAAGCTCCTACATTAGCTATGCAGACTCCGTC

CAGGGAAGGTTCACCATCTCTCGCGATAACGGCAAGAACAGCCTGTAT

CTGCAGATGAACAGCCTGCGAGCAGAGGACACAGCCCTGTACTTCTGT

GCCAGAGAATATGACTTCTGGTCCGCCTATTACGACGCCTTCGATGTC

TGGGGACAGGGGACTATGGTCACTGTCTCAAGC

The amino acid sequence of heavy chain variable region of MAB1 (123aa):

(SEQ ID NO: 2)
EVQLVESGGGLVQPGRSLRLSCAASGFTFSSYSMNWVRQAPGKGLEWV

SGISSSSSYISYADSVQGRFTISRDNGKNSLYLQMNSLRAEDTALYFC

AREYDFWSAYYDAFDVWGQGTMVTVSS

The nucleotide sequence of light chain variable region of MAB1 (333bp):

(SEQ ID NO: 3)
CAGAGCGAACTGACTCAGCCAAGAAGCGTCAGTGGATCACCTGGCCAG

AGCGTGACAATCTCCTGCACCGGCACAAGCAGGAACATTGGCGGGGGA

AATGACGTCCACTGGTACCAGCAGCATCCAGGGAAGGCCCCCAAACTG

CTGATCTCCGGAGTGATTGAGCGGAGCTCCGGCGTCCCCGATAGATTC

AGCGGGTCCAAGTCTGGAAACACAGCTTCTCTGACTATCAGTGGCCTG

CAGGCAGAGGACGAAGCCGATTACTATTGCCAGTCTTTCGACGGCAGT

CTGTCAGGGAGCGTGTTTGGCACTGGGACCGATGTGACCGTCCTG

The amino acid sequence of light chain variable region of MAB1 (111aa):

(SEQ ID NO: 4)
QSELTQPRSVSGSPGQSVTISCTGTSRNIGGGNDVHWYQQHPGKAPKL

LISGVIERSSGVPDRFSGSKSGNTASLTISGLQAEDEADYYCQSFDGS

LSGSVFGTGTDVTVL

2. Expression and Purification

The cDNA sequences of heavy chain (SEQ ID NO: 1 with a constant region of Ig gamma-1 chain C region, ACCESSION: P01857) and light chain (SEQ ID NO: 3 with a constant region of Ig lambda-2 chain C region; ACCESSION: P0CG05.1) of MAB1 were cloned into pUC57simple vector to obtain plasmid pUC57simple-MAB1H and pUC57simple-MAB1L, respectively.

The pUC57simple-MAB1H and pUC57simple-MAB1L were individually digested using HindIII and EcoRI, and recovered gene fragments of heavy and light chains from gel electrophoresis were sub-cloned into pcDNA3.1 vector respectively. The two recombinant plasmids were co-transfected into 293F cells. 7 days after transfection, the culture medium was processed by high-speed centrifugation and concentration, and applied onto Hitrap MabSelect SuRe column. MAB1 was eluted using Elution Buffer and buffer exchanged into PBS.

The purified MAB1 was examined on SDS-PAGE after boiling with reduced or non-reduced loading buffer. As shown in FIG. 1, the reduced MAB1 appeared at 45 kD (heavy chain) and 30 kD (light chain), while non-reduced MAB1 (entire antibody) appeared at 150 kD.

The obtained MAB1 in this example is used in the examples 4-9 below.

Example 4: Binding Kinetics Between MAB1 and Antigen PCSK9-his

The binding kinetics between MAB1 and antigen PCSK9-his were measured by Fortebio Octet System.

The MAB1 (Prepared in example 3) was immobilized to AR2G Biosensors by standard amine coupling procedures. After blocking the redundant amino groups with ethanolamine and equilibrating in PBST, binding affinities of MAB1 to antigen PCSK9-his were measured. The concentrations of PCSK9 were 411, 205.5, 102.8, 51.4, 25.7, 12.8, and 0 nM in PBST. The dissociation of antigen and antibody were also in PBST.

Figure 2:
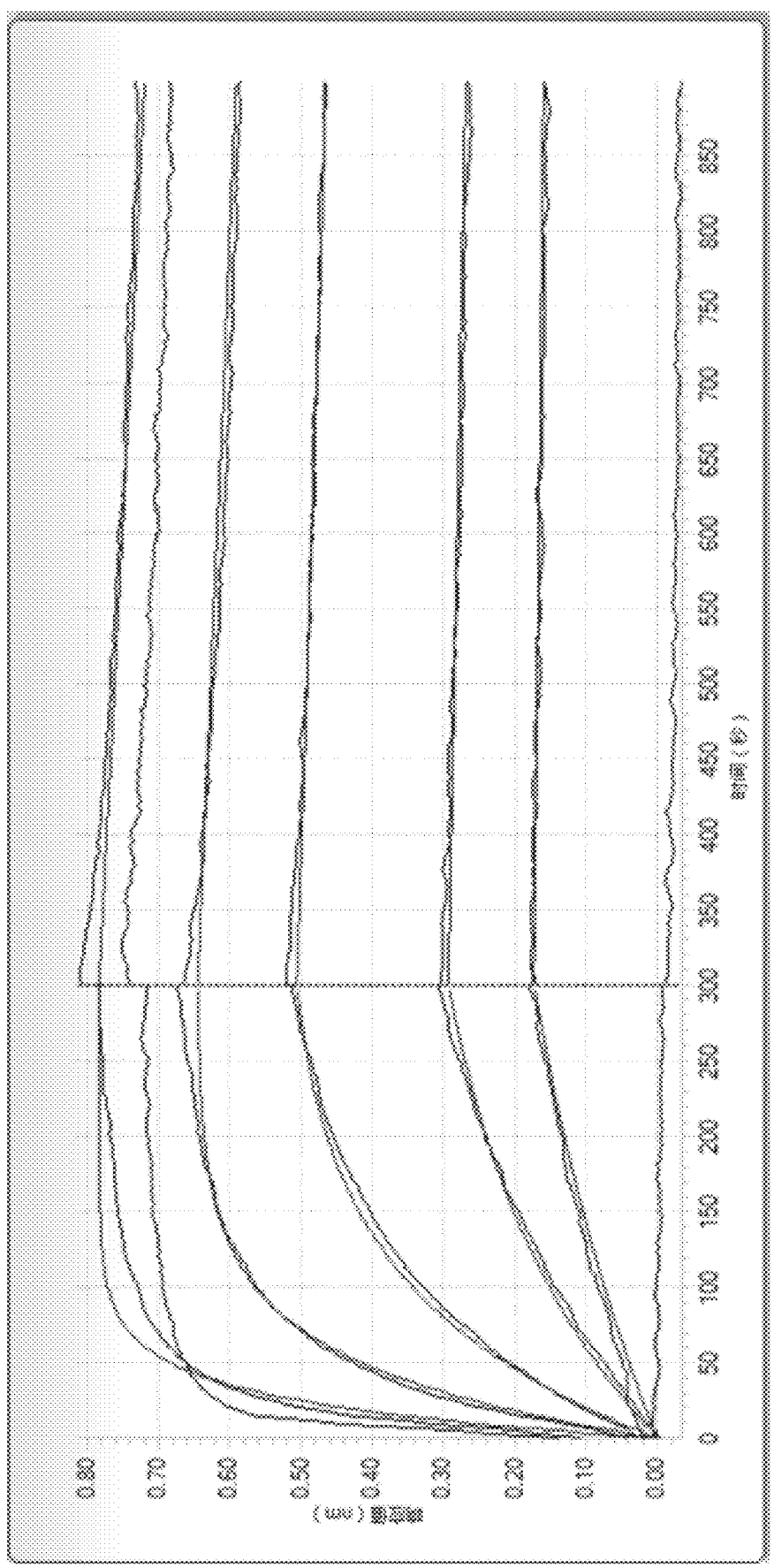
FIG. 2: Binding kinetics of MAB 1.

Binding kinetics between MAB1 and antigen PCSK9-his are shown in Table 2 and FIG. 2.

TABLE 2

Binding kinetics of MAB1

| Antibody | $K_D$ (M) | Kon (1/Ms) | Kon Error | Kdis (1/s) | Kdis Error |
|---|---|---|---|---|---|
| MAB1 | 7.19E−10 | 2.00E+05 | 2.08E+03 | 1.44E−04 | 5.11E−06 |

$K_D$: Dissociation constant; Kon: Binding rate of antigen and antibody; Kdis: Dissociation rate of antigen and antibody; $K_D$ = Kdis/Kon.

Evidently, antibody MAB1 has good binding affinity with PCSK9.

Example 5: Binding Activities of MAB1 to PCSK9

Figure 3:
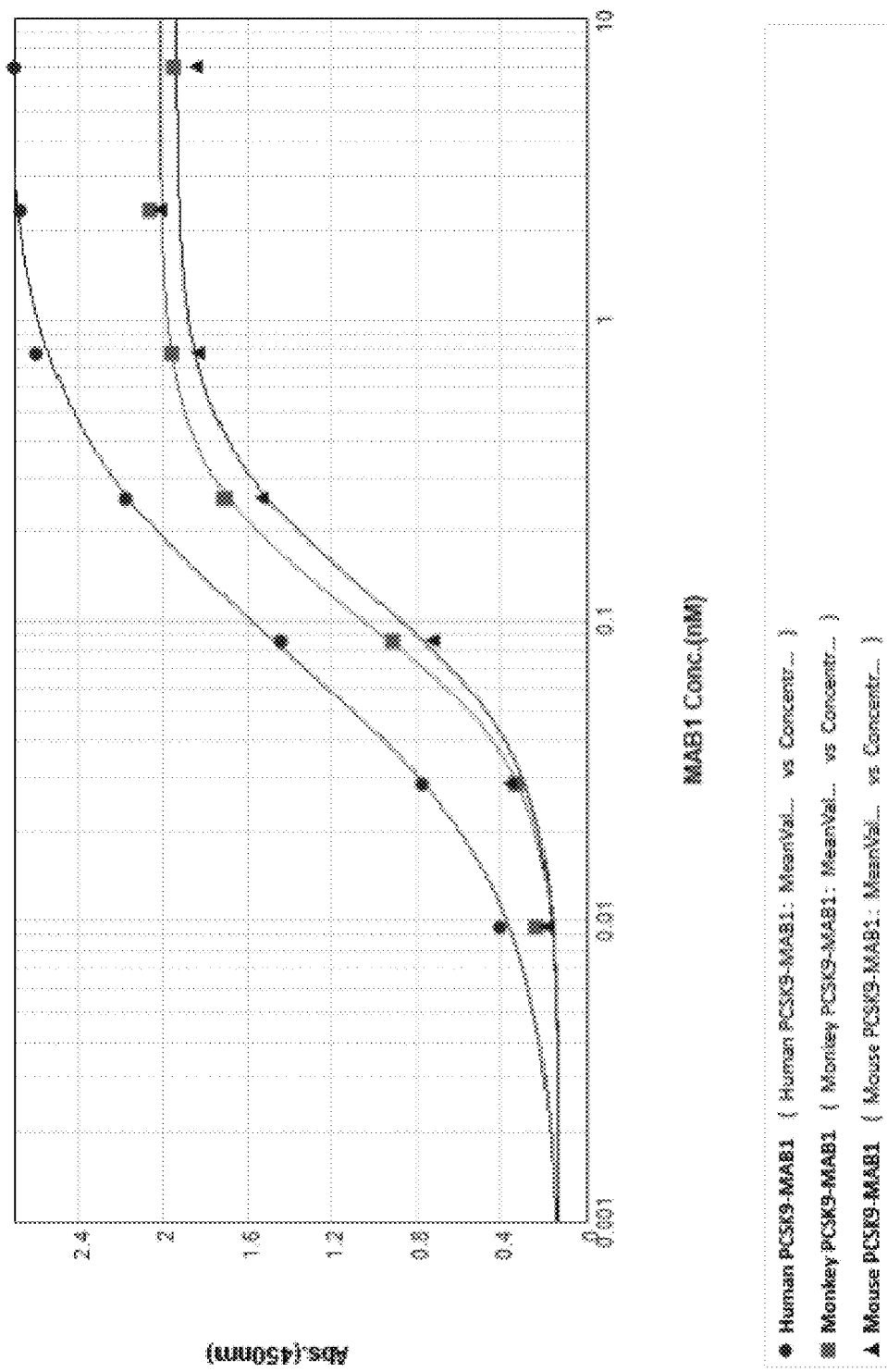
FIG. 3: ELISA results of MAB1 binding to human, mouse, and monkey PCSK9.

1. Measure binding activities of MAB1 to mouse, monkey, and human PCSK9 (Prepared in Example 1) by Sandwich ELISA After the microplate coated with mouse anti-his monoclonal antibody (GenScript, A00186) was blocked with BSA for 2 hours, mouse, monkey, and human antigen PCSK9 were added separately and incubated for 30 mins, then MAB1 was added and incubated for 30mins. HRP-labeled secondary antibody (goat anti-hIgG antibody) (Jackson, 109-035-088) was added with TMB (Neogen, 308177) into each well and developed for 5 mins, the absorbance values were read at a wavelength of 450 nm (shown in FIG. 3).

Evidently, MAB1 can bind to PCSK9 effectively with dose-dependency.

Absorbance values are shown in Tables 3-5 for MAB1 at different diluted concentrations to bind mouse, monkey, and human antigen PCSK9.

TABLE 3

Binding of MAB1 to mouse PCSK9 by sandwich ELISA

| Antibody concentration | Coating: Mouse anti-His (2 µg/mL, 50 µL/well) Antigen: mouse PCSK9-his (0.25 µg/mL, 100 µL/well) | |
|---|---|---|
| (µg/mL) | OD1 (450 nm) | OD2 (450 nm) |
| 1 | 1.750 | 1.932 |
| 0.3 | 1.940 | 2.077 |
| 0.1 | 1.895 | 1.773 |
| 0.03 | 1.554 | 1.525 |
| 0.01 | 0.739 | 0.719 |
| 0.003 | 0.407 | 0.310 |
| 0.001 | 0.179 | 0.195 |
| PBS | 0.067 | 0.076 |
| Secondary antibody | HRP labeled Goat anti-human IgG (1:5000) | |

TABLE 4

Binding of MAB1 to monkey PCSK9 by sandwich ELISA

| Antibody concentration | Coating: Mouse anti-His (2 µg/mL, 50 µL/well) Antigen: monkey PCSK9-his (0.125 µg/mL, 100 µL/well) | |
|---|---|---|
| (µg/mL) | OD1 (450 nm) | OD2 (450 nm) |
| 1 | 1.961 | 1.927 |
| 0.3 | 2.066 | 2.058 |
| 0.1 | 1.933 | 1.984 |
| 0.03 | 1.755 | 1.653 |
| 0.01 | 0.973 | 0.866 |
| 0.003 | 0.290 | 0.363 |
| 0.001 | 0.237 | 0.225 |
| PBS | 0.072 | 0.074 |
| Secondary antibody | HRP labeled Goat anti-human IgG (1:5000) | |

TABLE 5

Binding of MAB1 to human PCSK9 by sandwich ELISA

| Antibody concentration | Coating: Mouse anti-His (2 µg/mL, 50 µL/well) Antigen: Human PCSK9-his (0.25 µg/mL, 100 µL/well) | |
|---|---|---|
| (µg/mL) | OD1 (450 nm) | OD2 (450 nm) |
| 1 | 1.961 | 1.927 |
| 0.3 | 2.066 | 2.058 |
| 0.1 | 1.933 | 1.984 |
| 0.03 | 1.755 | 1.653 |
| 0.01 | 0.973 | 0.866 |
| 0.003 | 0.290 | 0.363 |
| 0.001 | 0.237 | 0.225 |
| PBS | 0.072 | 0.074 |
| Secondary antibody | HRP labeled Goat anti-human IgG (1:5000) | |

$EC_{50}$ were then obtained through Curve Simulation (Table 6), using quantitative analyses of absorbance values.

TABLE 6

$EC_{50}$ of MAB1 to PCSK9 measured by sandwich ELISA

| | $EC_{50}$ (nM) | | |
|---|---|---|---|
| Antibody | Human PCSK9 | Monkey PCSK9 | Mouse PCSK9 |
| MAB1 | 0.081 | 0.103 | 0.124 |

Evidently, MAB1 can bind effectively to human, mouse, and monkey PCSK9.

2. Measure Binding Activities of MAB1 with Human PCSK9 Against LDLR by Competition ELISA.

LDLR-His (prepared in example 2) was allowed to bind to the microtiter plate at 4° C. overnight. After the plate was blocked with 1% BSA at 37° C. for 2 h, a mixture of human PCSK9 and MAB1 (concentration as shown in Table 7) was added and incubated at 37° C. for 30 mins, then peroxidase-conjugated secondary goat anti-human IgG was added at 37° C. and incubated for 60 minutes. The plates were washed three times with PBS, and the peroxidase substrates were added. The reaction was terminated and the absorbance was determined at 450 nM using a microplate reader (Table 7).

Figure 4:
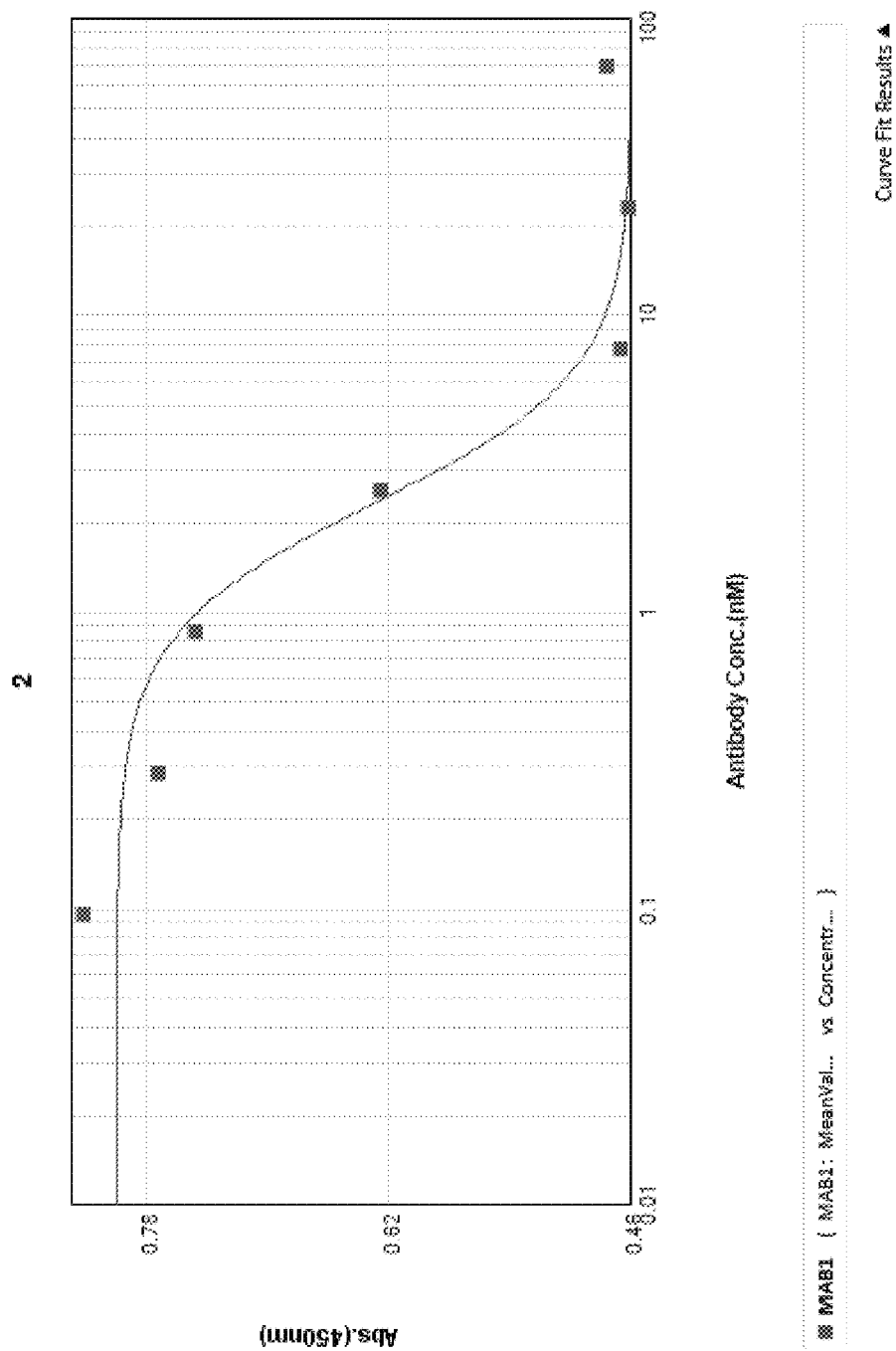
FIG. 4: Competition ELISA results of MAB1 binding to human PCSK9 against LDLR.

The binding activity of MAB1 to PCSK9 against LDLR (prepared in example 2) were shown in FIG. 4, which demonstrated that MAB1 could block the association of PCSK9 with LDLR effectively with dose-dependency.

The absorbance values of different doses were shown in Table 7, which indicated that MAB1 can inhibit the reduction of LDLR on cell membrane through binding to PCSK9 (i.e., MAB1 can block the binding of PCSK9 to LDLR and the internalization and degradation of LDLR); this inhibition is dose dependent.

TABLE 7

Competitive binding of MAB1 with PCSK9 against LDLR

| Antibody concentration | Coating: LDLR-His (2 µg/mL, 50 µL/well) Antigen: Human PCSK9-His-biotin (1 µg/mL) | |
|---|---|---|
| (µg/mL) | OD1 (450 nm) | OD2 (450 nm) |
| 10 | 0.460 | 0.491 |
| 3 | 0.452 | 0.469 |
| 1 | 0.472 | 0.460 |
| 0.3 | 0.616 | 0.633 |
| 0.1 | 0.761 | 0.734 |
| 0.03 | 0.749 | 0.796 |

TABLE 7-continued

| Competitive binding of MAB1 with PCSK9 against LDLR | | |
|---|---|---|
| Antibody concentration | Coating: LDLR-His (2 μg/mL, 50 μL/well) Antigen: Human PCSK9-His-biotin (1 μg/mL) | |
| (μg/mL) | OD1 (450 nm) | OD2 (450 nm) |
| 0.01 | 0.843 | 0.801 |
| PBS | 0.730 | 0.878 |
| Secondary antibody | SA-HRP (1:4000) | |

$EC_{50}$ were calculated to be 2.339 nM through Curve Simulation using quantitative analyses of absorbance values. Evidently, MAB1 can competitively bind to PCSK9 against LDLR, inhibit PCSK9-induced reduction of LDLR on cell surface (details in example 6 below), and regulate the metabolism of LDL cholesterol in vivo (i.e., MAB1 down-regulates the level of LDL cholesterol in serum, as shown in example 7 below).

Example 6: Cellular Activity of MAB1

Flow cytometry and western blot were used to measure the effect of MAB1 on the level of LDLR on human liver cell line HepG2 surface.

1. FACS Measurement of LDLR Level on HepG2 Surface Regulated by MAB1

After removing cell culture medium, healthy HepG2 cells were incubated with PCSK9 and antibodies at the concentrations described in Table 8 for 24 hours and 48 hours separately.

After incubation for 24 hours or 48 hours, the cells were collected by conventional enzyme digestion with $2\times10^5$ cells in each tube. PE labeled Rabbit anti-hLDLR (diluted 200 fold with 1% PBSA) was added into each tube, and incubated on ice for 1 hr. The cells were washed with PBS twice and resuspended in 300 μL PBS. The PE fluorescent signal was measured by a flow cytometer.

Figure 5:
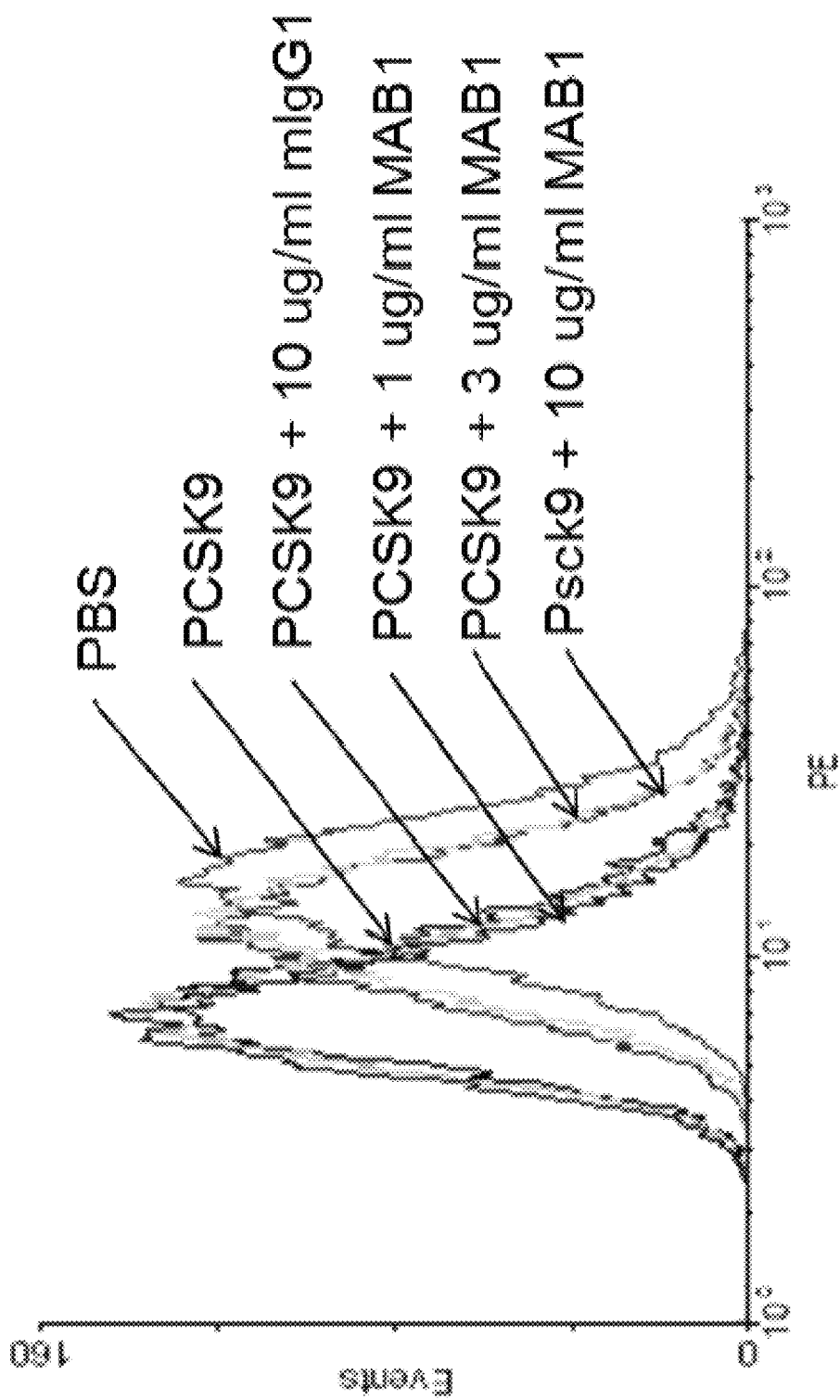
FIG. 5: FACS detection of LDLR on human HepG2 cell surface after incubation with MAB1 for 24 hours.
Figure 6:
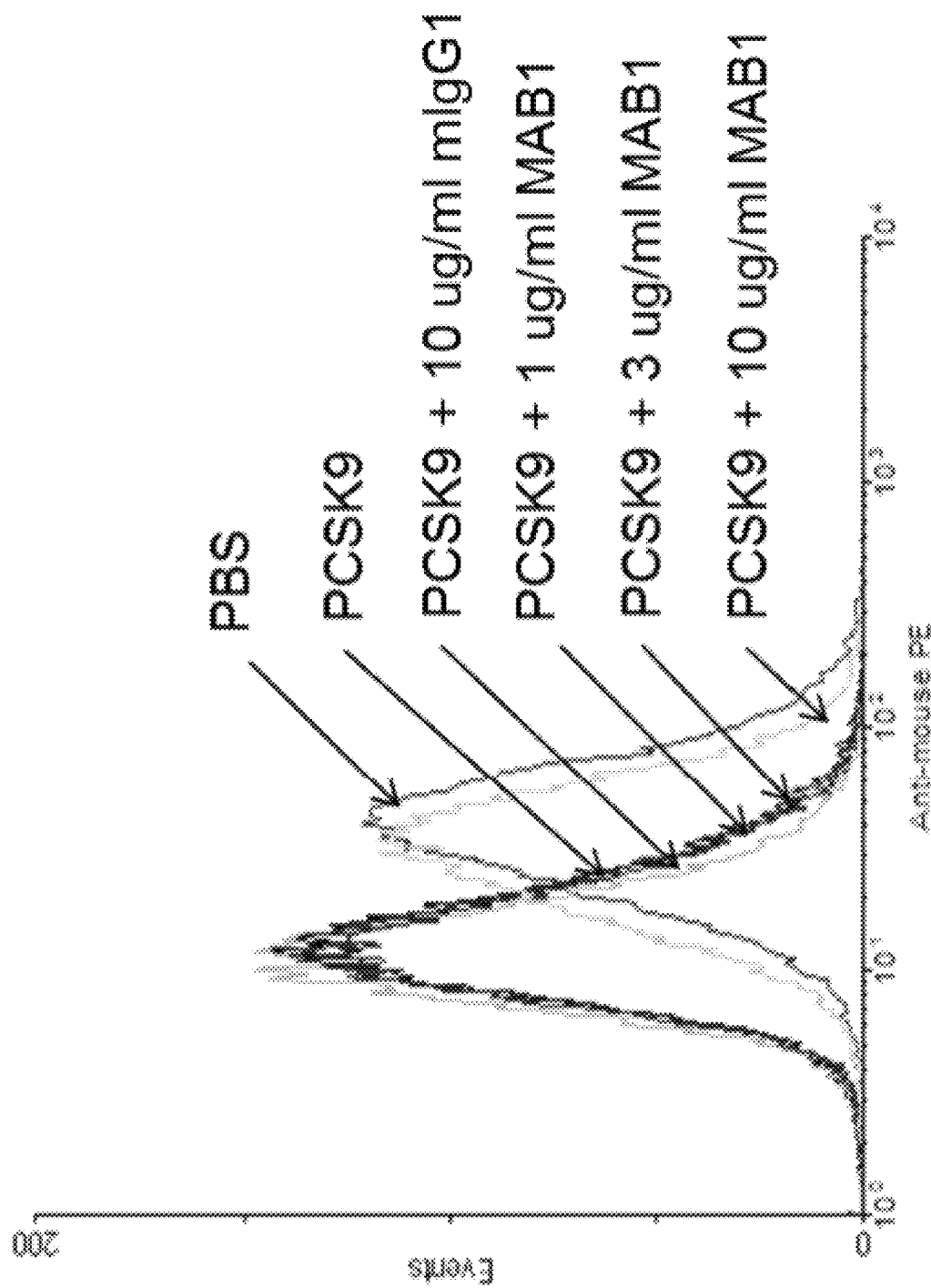
FIG. 6: FACS detection of LDLR on human HepG2 cell surface after incubation with MAB1 for 48 hours.

The results after 24 hours and 48 hours were shown in FIG. 5 and FIG. 6 respectively. Evidently, MAB1 blocked the PCSK9-induced reduction of LDLR on the cell surface in a dose dependent manner, and prevented the negative regulation of LDLR by PCSK9 effectively.

TABLE 8

| Concentrations of antibodies and PCSK9 antigen | | | | | | |
|---|---|---|---|---|---|---|
| Samples | 1 | 2 | 3 | 4 | 5 | 6 |
| PCSK9 (μg/mL) | 0 | | | 3 | | |
| Antibody | | mIgG1 (negative control) | | | MAB1 | |
| Antibody Conc. (μg/mL) | 0 | 0 | 10 | 1 | 3 | 10 |

2. WB Measurement of LDLR Level on HepG2 Surface Regulated by MAB1

Figure 7:
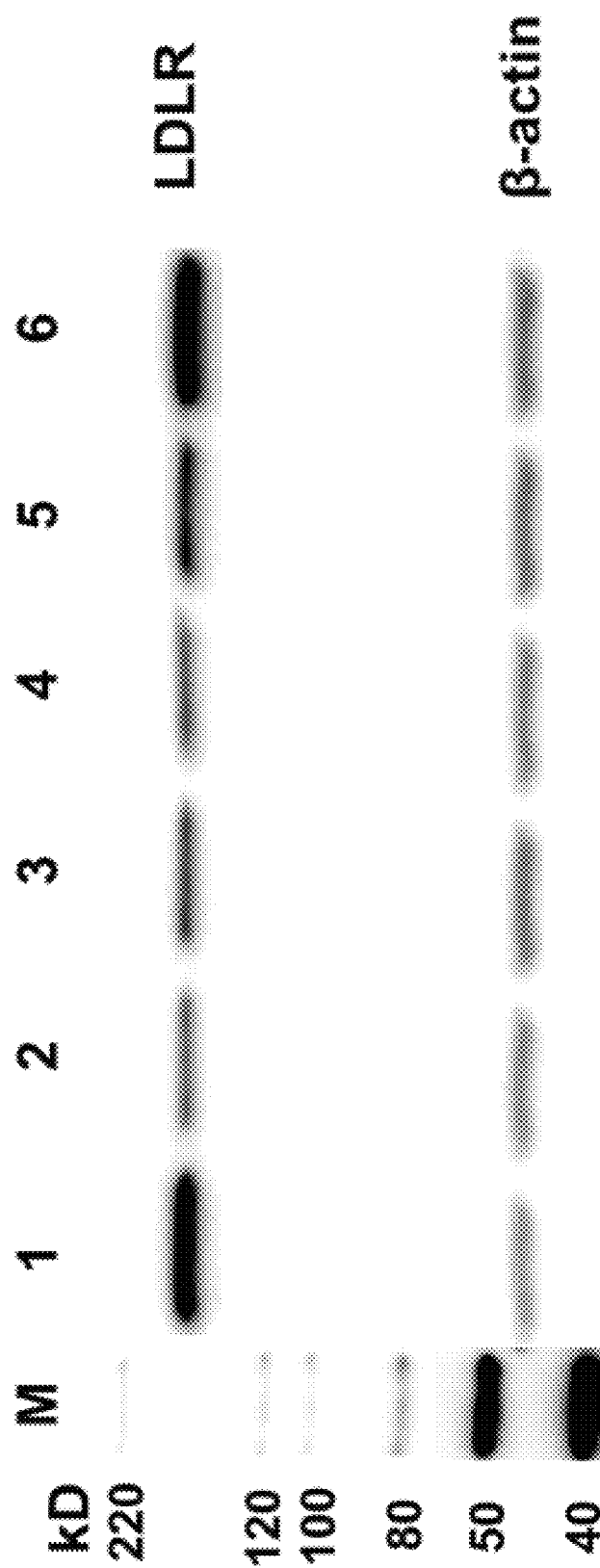
FIG. 7: SDS-PAGE results of LDLR on human HepG2 cell surface after incubation with MAB1 for 24 hours.

After removing cell culture medium, HepG2 cells were incubated with PCSK9 and antibodies at concentrations described in Table 8 for 24 hours. Cells were collected and lysed, and the supernatant was examined with SDS-PAGE. As shown in FIG. 7, the target protein should appear at about 140 kD. The data showed that MAB1 could upregulate the level of LDLR in a dose dependent manner, and prevent effectively the negative regulation of LDLR by PCSK9.

Example 7: Effect of MAB1 on Low Density Lipoprotein Cholesterol (LDL-C) In Vivo 1. Effect of MAB1 on Serum LDL-C in Mice.

To investigate the effect of MAB1 on serum LDL-C, mice were randomly assigned into 4 groups for subcutaneous injections:
 Control group (saline, administered as 10 mL/kg, n=8)
 MAB1 60 mg/kg group (MAB1 60 mg/kg, administered as 10 mL/kg, n=6)
 MAB 1 90 mg/kg group (MAB1 90 mg/kg, administered as 20 mL/kg, n=6)
 Evolocumab 60 mg/kg group (Evolocumab 60 mg/kg, administered as 10 mL/kg, n=4).

Blood samples (150 μl) of each mouse were collected from inner canthal veins at pre-dose, 3 days, 7 days, 10 days, 18 days, 24 days, and 32 days after administration, which were centrifuged at 4500 rpm for 10 mins after collection to isolate the serum. LDL-C levels in the serum were then measured by Mindray BS-180 Automatic biochemical analyzer with LDL-C assay kit purchased from Shenzhen Mindray Bio-Medical Electronics Co., Ltd.

Figure 8:
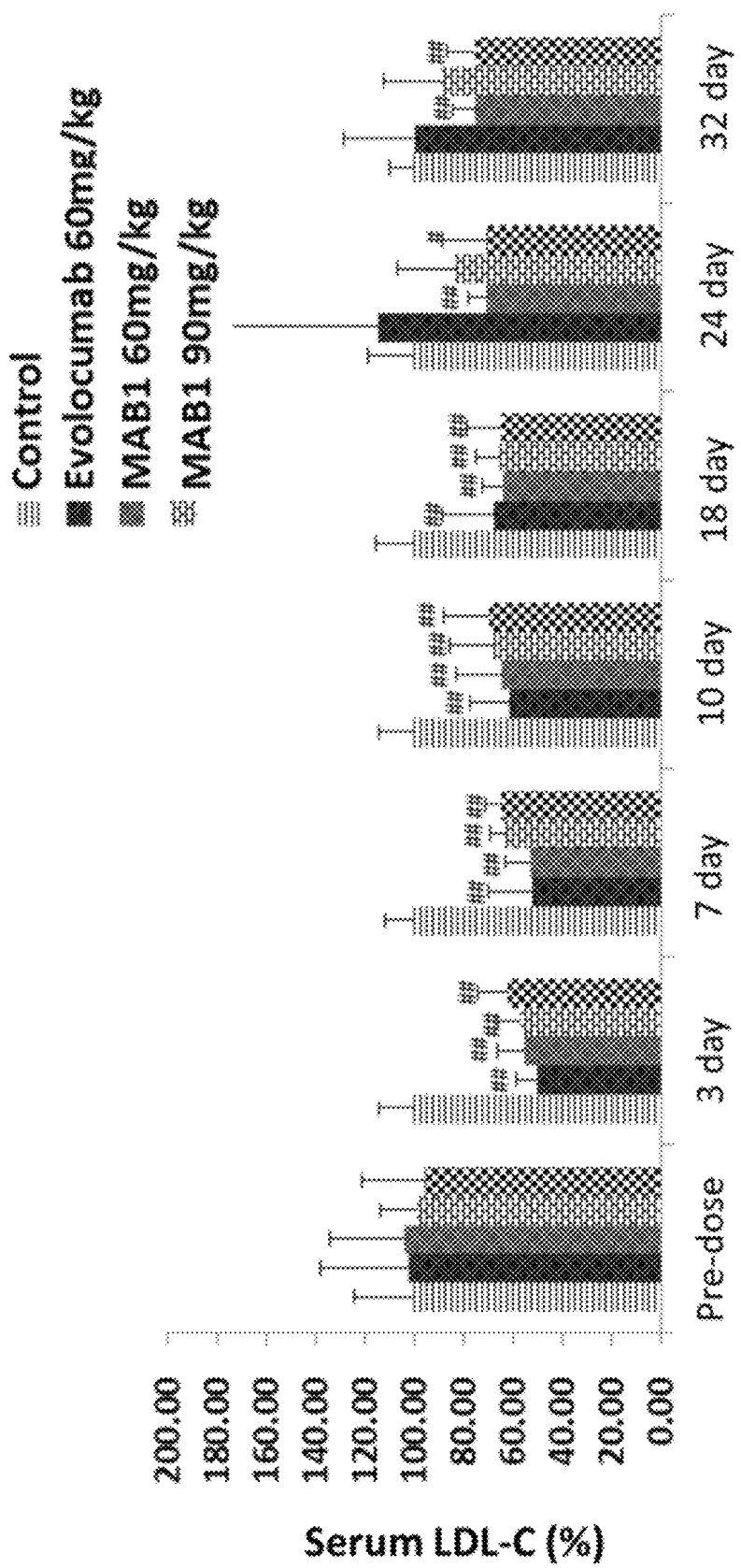
FIG. 8: Effects of anti-PCSK9 antibodies MAB1 and Evolocumab on concentrations of LDL-C in mouse serum.

As shown in FIG. 8, MAB1 started reducing serum LDL-C levels at 3 days in mice, indicating an efficacy equivalent to Evolocumab, and MAB1 displayed a longer efficacious period (32 days) than Evolocumab (18 days).

2. Effect of MAB1 on Serum LDL-C in Monkeys.

To investigate the effect of MAB1 on serum LDL-C, 4 cynomolgus monkeys were randomly assigned into 2 groups for subcutaneous injections:
 MAB1 3 mg/kg group (MAB1 3 mg/kg, n=2)
 MAB1 18 mg/kg group (MAB1 18 mg/kg, n=2).

The pre-dose serum LDL-C levels were used as Control. Blood samples of each monkey were collected at pre-dose, 30 mins, 5 hours, 1 day, 5 days, 7 days, 9 days, 11 days, 13 days, 15 days, 17 days, 19 days, and 21 days after administration, which were centrifuged at 3000 rpm for 10 mins after collection to isolate the serum. LDL-C levels in the serum were then measured by Mindray BS-180 Automatic biochemical analyzer with LDL-C assay kit purchased from Shenzhen Mindray Bio-Medical Electronics Co., Ltd.

Figure 9:
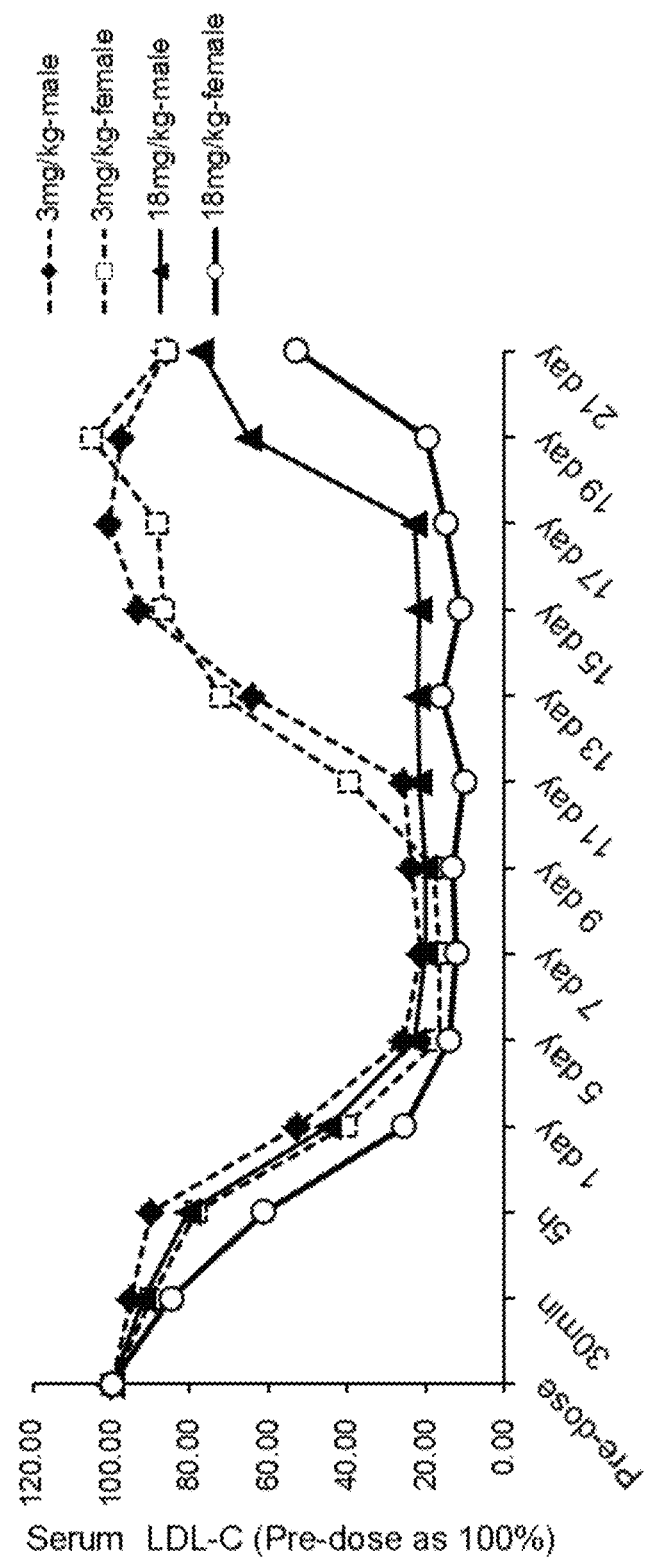
FIG. 9: Effect of anti-PCSK9 antibody MAB1 on concentration of LDL-C in monkey serum.

As shown in FIG. 9, MAB1 at dosages of 3 mg/kg and 18 mg/kg reduced serum LDL-C levels in monkeys, and MAB1 at the dosage of 18 mg/kg displayed a long efficacious period (17 days) in cynomolgus monkeys.

Example 8: Effect of MAB1 on High Density Lipoprotein Cholesterol (HDL-C) In Vivo 1. Effect of MAB1 on Serum HDL-C in Mice To investigate the effect of MAB1 on serum HDL-C, mice were randomly assigned into 5 groups for subcutaneous injections:
 Control group (saline, administered as 10 mL/kg, n=8)
 MAB1 60 mg/kg group (MAB1 60 mg/kg, administered as 10 mL/kg, n=6)
 MAB1 90 mg/kg group (MAB1 90 mg/kg, administered as 20 mL/kg, n=6)
 MAB1 120 mg/kg group (MAB1 120 mg/kg, administered as 20 mL/kg, n=3)
 Evolocumab 60 mg/kg group (Evolocumab 60 mg/kg, administered as 10 mL/kg, n=4).

Blood samples (15 μl) of each mouse were collected from inner canthal veins at pre-dose, 3 days, 7 days, 10 days, 18 days, 24 days, and 32 days after administration, which were centrifuged at 4500 rpm for 10 mins after collection to isolate the serum. HDL-C levels in the serum were then measured by Mindray BS-180 Automatic biochemical analyzer with HDL-C assay kit purchased from Shenzhen Mindray Bio-Medical Electronics Co., Ltd.

Figure 10:
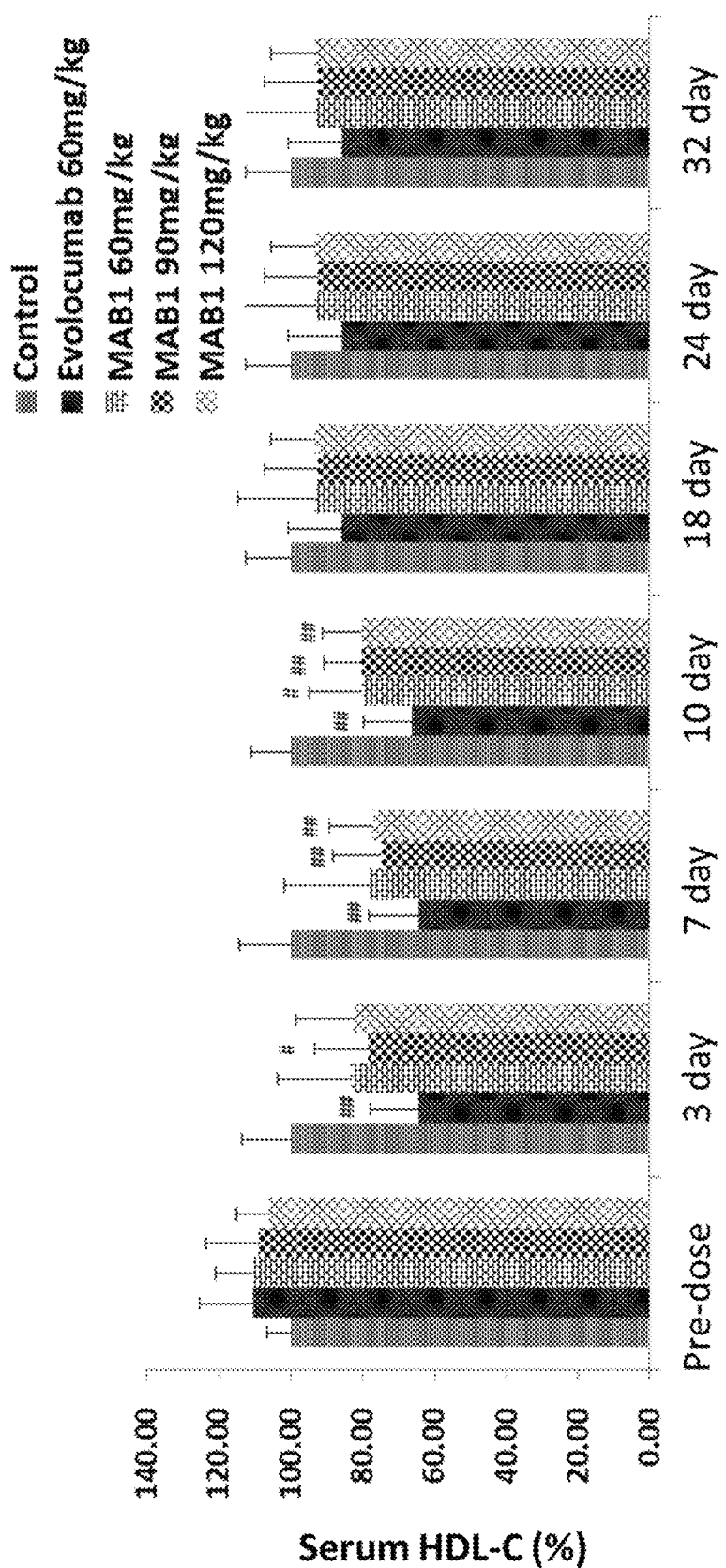
FIG. 10: Effects of anti-PCSK9 antibodies MAB1 and Evolocumab on concentrations of HDL-C in mouse serum.

As shown in FIG. 10, MAB1 reduced the serum HDL-C levels at 3 days in mice, the same as Evolocumab. After 10 days, the serum HDL-C levels recovered to the same as those of the control group.

2. Effect of MAB1 on Serum HDL-C in Monkeys.

To investigate the effect of MAB1 on serum HDL-C, 4 cynomolgus monkeys were randomly assigned into 2 groups for subcutaneous injections:

MAB1 3 mg/kg group (MAB1 3 mg/kg, n=2)
MAB1 18 mg/kg group (MAB1 18 mg/kg, n=2).

The pre-dose serum HDL-C levels were used as Control. Blood samples of each monkey were collected at pre-dose, 30 mins, 5 hours, 1 day, 5 days, 7 days, 9 days, 11 days, 13 days, 15 days, 17 days, 19 days, and 21 days after administration, which were centrifuged at 3000 rpm for 10 mins after collection to isolate the serum. HDL-C levels in the serum were then measured by Mindray BS-180 Automatic biochemical analyzer with HDL-C assay kit purchased from Shenzhen Mindray Bio-Medical Electronics Co., Ltd.

Figure 11:
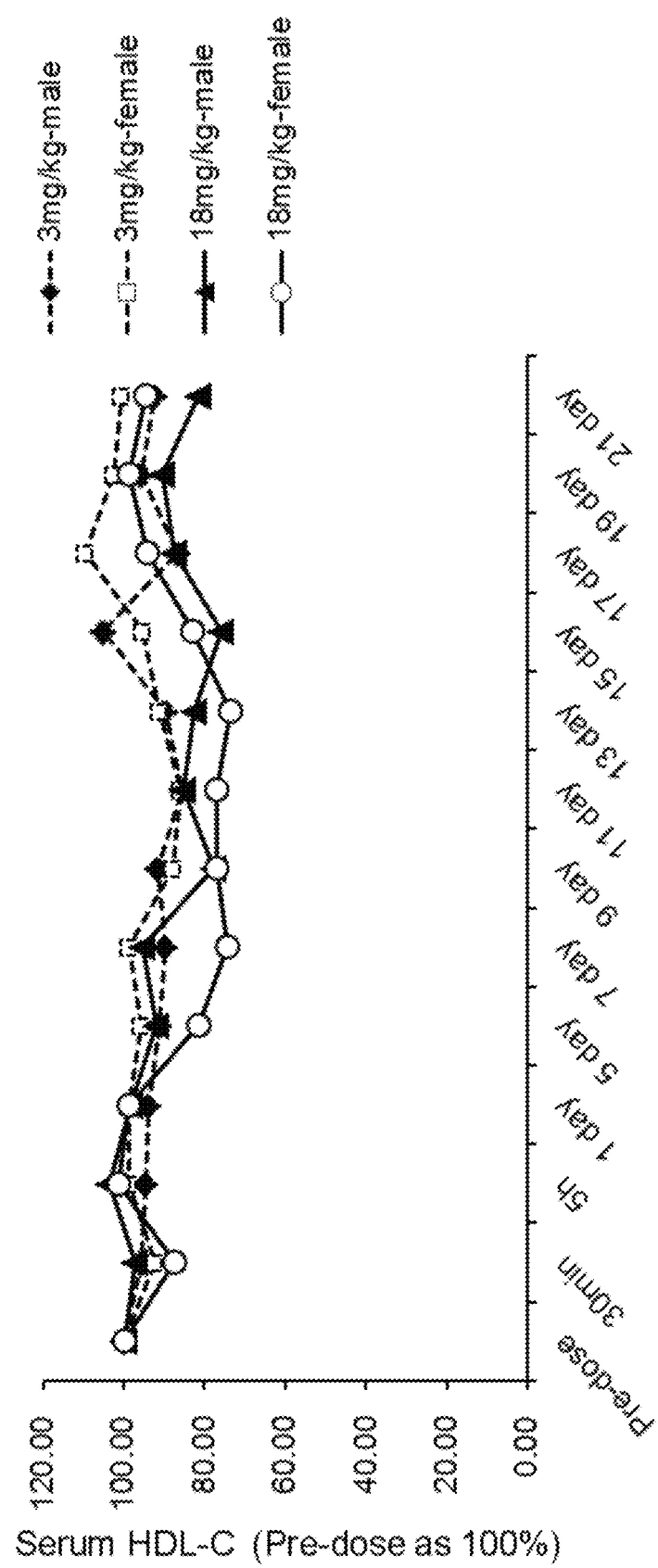
FIG. 11: Effect of anti-PCSK9 antibody MAB1 on concentration of HDL-C in monkey serum.

As shown in FIG. 11, MAB1 at dosages of 3 mg/kg and 18 mg/kg showed no effect on serum HDL-C in cynomolgus monkeys.

Example 9. Effect of MAB1 on Triglyceride (TG) In Vivo

1. Effect of MAB1 on Serum Triglyceride (TG) in Mice.

To investigate the effect of MAB1 on serum triglyceride, mice were randomly assigned into 4 groups for subcutaneous injections:

Control group (saline, administered as 10 mL/kg, n=8)
MAB1 60 mg/kg group (MAB1 60 mg/kg, administered as 10 mL/kg, n=6)
MAB1 90 mg/kg group (MAB1 90 mg/kg, administered as 20 mL/kg, n=6)
Evolocumab 60 mg/kg group (Evolocumab 60 mg/kg, administered as 10 mL/kg, n=4).

Blood samples (150 µl) of each mouse were collected from inner canthal veins at pre-dose, 3 days, 7 days, 10 days, 18 days, 24 days, and 32 days after administration, which were centrifuged at 4500 rpm for 10 mins after collection to isolate the serum. Triglyceride levels in the serum were then measured by Mindray BS-180 Automatic biochemical analyzer with triglyceride assay kit purchased from Shenzhen Mindray Bio-Medical Electronics Co., Ltd.

Figure 12:
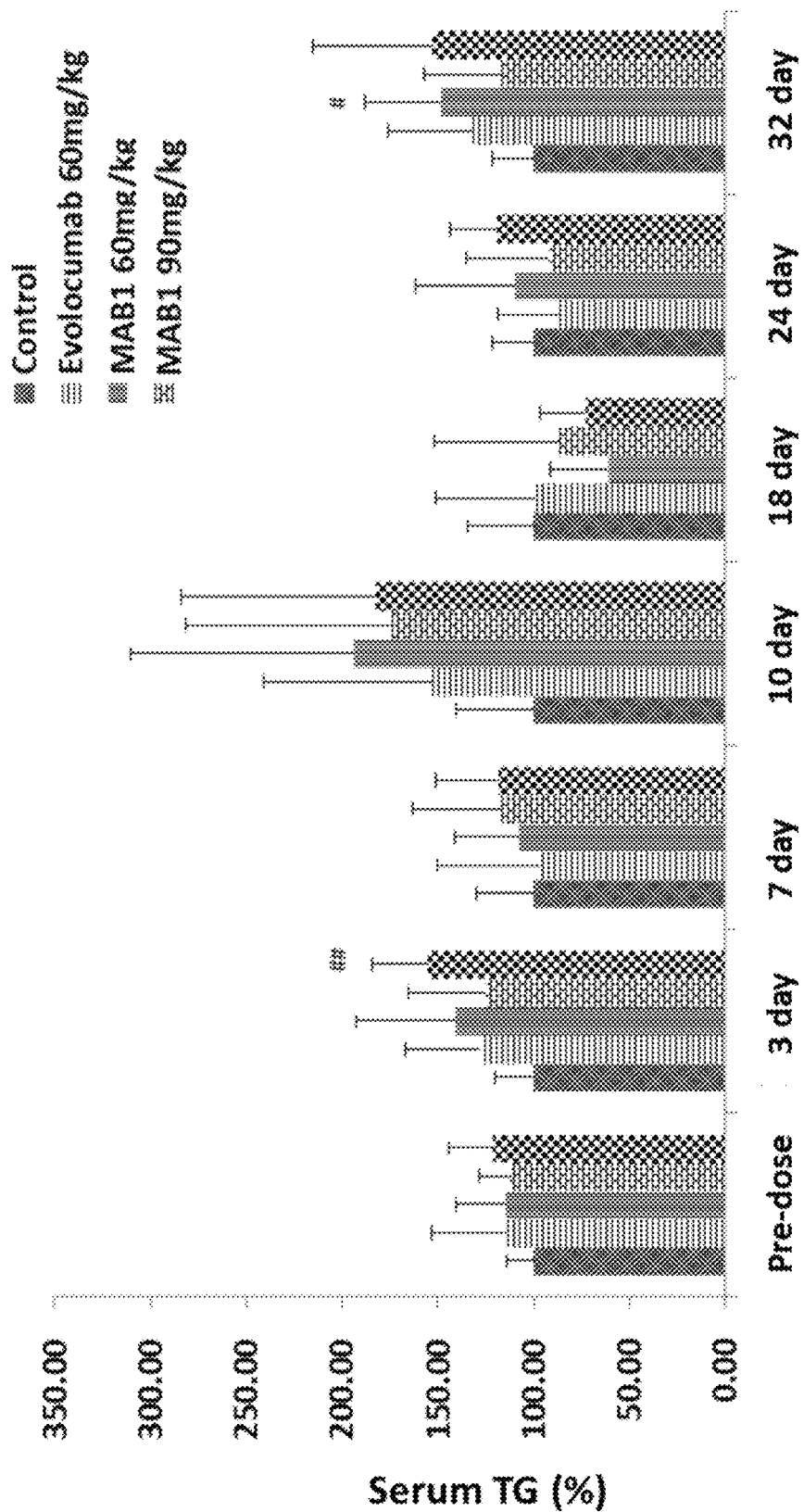
FIG. 12: Effects of anti-PCSK9 antibodies MAB1 and Evolocumab on concentration of TG in mouse serum.

As shown in FIG. 12, MAB1 boosted the serum triglyceride levels after 3 days in mice at high dosage (90 mg/kg), after 32 days at low dosage (60 mg/kg), and there was no difference from the control group at other time points.

2. Effect of MAB1 on Serum Triglyceride (TG) in Monkeys.

To investigate the effect of MAB1 on serum triglyceride, 4 cynomolgus monkeys were randomly assigned into 2 groups for subcutaneous injections:

MAB1 3 mg/kg group (MAB1 3 mg/kg, n=2)
MAB1 18 mg/kg group (MAB1 18 mg/kg, n=2).

The pre-dose serum triglyceride levels were used as Control. Blood samples of each monkey were collected at pre-dose, 30 mins, 5 hours, 1 day, 5 days, 7 days, 9 days, 11 days, 13 days, 15 days, 17 days, 19 days, and 21 days after administration, which were centrifuged at 3000 rpm for 10 mins after collection to isolate the serum. Triglyceride levels in the serum were then measured by Mindray BS-180 Automatic biochemical analyzer with triglyceride assay kit purchased from Shenzhen Mindray Bio-Medical Electronics Co., Ltd.

Figure 13:
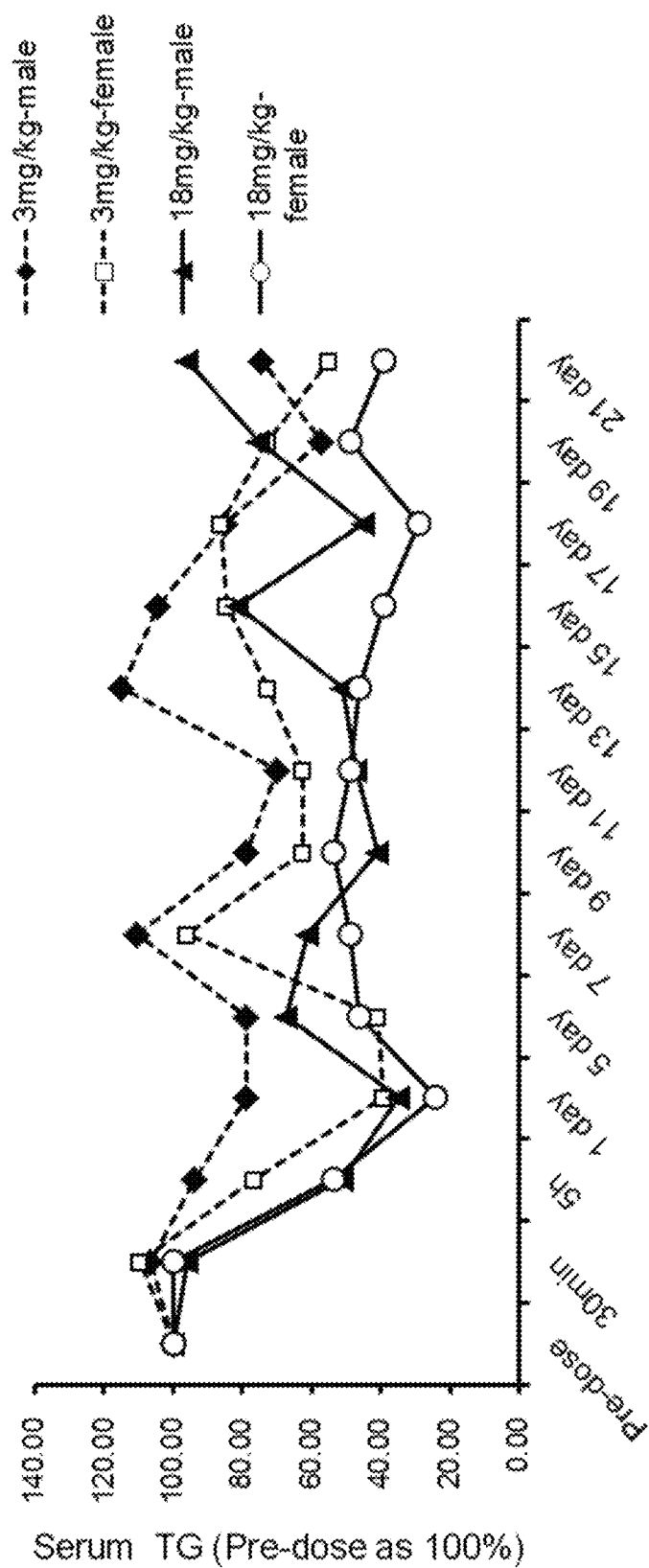
FIG. 13: Effect of anti-PCSK9 antibody MAB1 on concentration of TG in monkey serum.

As shown in FIG. 13, MAB1 at a dosage of 18 mg/kg reduced the serum triglyceride in cynomolgus monkeys for as long as 13 days after administration.

Although specific embodiments of the present invention have been described in detail, as will be appreciated by one skilled in the art, these details may incur various modifications and substitutions according to all the teachings we have disclosed. These changes are all covered by the scope of the present invention. The full scope of the present invention is given by the appended claims and any equivalents.

What is claimed is:

1. A synthetic polynucleotide comprising a sequence encoding a heavy chain variable region (VH), wherein the heavy chain variable region comprises complementary determining regions (CDRs) having amino acid sequences of SEQ ID NOs: 5-7.

2. The synthetic polynucleotide of claim 1, wherein the heavy chain variable region has the amino sequence of SEQ ID NO: 2.

3. An expression vector, wherein the expression vector comprises the synthetic polynucleotide of claim 1.

4. The expression vector of claim 3, wherein the expression vector is selected from the group consisting of a plasmid, a cosmid, an artificial chromosome, a phage, and a virus.

5. A host cell, wherein the host cell comprises the synthetic polynucleotide of claim 1.

6. The host cell of claim 5, wherein the host cell is selected from the group consisting of a prokaryotic cell, an insect cell, an animal cell, and a human cell.

7. A method to producing a monoclonal antibody, the method comprising growing at least one host cell of claim 5 under suitable conditions and recovering monoclonal antibodies from the cell culture.

8. A synthetic nucleotide comprising a sequence encoding a light chain variable region (LH), wherein the light chain variable region comprises complementary determining regions (CDRs) having amino acid sequences of SEQ ID NOs: 8-10.

9. The synthetic nucleotide of claim 8, wherein the light chain variable region has the amino sequence of SEQ ID NO: 4.

10. An expression vector, wherein the expression vector comprises the synthetic polynucleotide of claim 8.

11. The expression vector of claim 10, wherein the expression vector is selected from the group consisting of a plasmid, a cosmid, an artificial chromosome, a phage, and a virus.

12. A host cell, wherein the host cell comprises the synthetic polynucleotide of claim 8.

13. The host cell of claim 12, wherein the host cell is selected from the group consisting of a prokaryotic cell, an insect cell, an animal cell, and a human cell.

14. A method to producing a monoclonal antibody, the method comprising growing at least one host cell of claim 12 under suitable conditions and recovering monoclonal antibodies from the cell culture.

15. A composition comprising:
  a synthetic polynucleotide comprising a sequence encoding a heavy chain variable region (VH), wherein the heavy chain variable region comprises complementary determining regions (CDRs) having amino acid sequences of SEQ ID NOs: 5-7, and
  a synthetic polynucleotide comprising a sequence encoding a light chain variable region (LH), wherein the light chain variable region comprises complementary determining regions (CDRs) having amino acid sequences of SEQ ID NOs: 8-10.

16. The composition of claim 15, wherein the heavy chain variable region has the amino sequence of SEQ ID NO: 2 and the light chain variable region has the amino sequence of SEQ ID NO: 4.

17. A host cell, wherein the host cell comprises the composition of claim 15.

18. The host cell of claim 17, wherein the host cell is selected from the group consisting of a prokaryotic cell, an insect cell, an animal cell, and a human cell.

19. A method to producing a monoclonal antibody, the method comprising growing at least one host cell of claim 17 under suitable conditions and recovering monoclonal antibodies from the cell culture.

* * * * *

SEQUENCE LISTING

<160> NUMBER OF SEQ ID NOS: 10

<210> SEQ ID NO 1
<211> LENGTH: 369
<212> TYPE: DNA
<213> ORGANISM: Artificial Sequence
<220> FEATURE:
<223> OTHER INFORMATION: DNA sequence for heavy chain variable region of
      monoclonal antibody MAB1

<400> SEQUENCE: 1

```
gaggtgcagc tggtggagtc tggaggaggc ctggtgcagc ccggaagatc tctgagactg      60
agttgcgccg cttcaggatt caccttagc tcctacagca tgaactgggt gcggcaggct     120
cctggcaagg ggctggagtg ggtctccgga atctctagtt caagctccta cattagctat     180
gcagactccg tccagggaag gttcaccatc tctcgcgata acggcaagaa cagcctgtat     240
ctgcagatga acagcctgcg agcagaggac acagccctgt acttctgtgc cagagaatat     300
gacttctggt ccgcctatta cgacgccttc gatgtctggg gacaggggac tatggtcact     360
gtctcaagc                                                             369
```

```
<210> SEQ ID NO 2
<211> LENGTH: 123
<212> TYPE: PRT
<213> ORGANISM: Artificial Sequence
<220> FEATURE:
<223> OTHER INFORMATION: Amino acid sequence for heavy chain variable
      region of monoclonal antibody MAB1

<400> SEQUENCE: 2

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Gly Ile Ser Ser Ser Ser Tyr Ile Ser Tyr Ala Asp Ser Val
    50                  55                  60

Gln Gly Arg Phe Thr Ile Ser Arg Asp Asn Gly Lys Asn Ser Leu Tyr
65                  70                  75                  80

Leu Gln Met Asn Ser Leu Arg Ala Glu Asp Thr Ala Leu Tyr Phe Cys
                85                  90                  95

Ala Arg Glu Tyr Asp Phe Trp Ser Ala Tyr Tyr Asp Ala Phe Asp Val
            100                 105                 110

Trp Gly Gln Gly Thr Met Val Thr Val Ser Ser
        115                 120

<210> SEQ ID NO 3
<211> LENGTH: 333
<212> TYPE: DNA
<213> ORGANISM: Artificial Sequence
<220> FEATURE:
<223> OTHER INFORMATION: DNA sequence for light chain variable region of
      monoclonal antibody MAB1

<400> SEQUENCE: 3
cagagcgaac tgactcagcc aagaagcgtc agtggatcac ctggccagag cgtgacaatc        60
tcctgcaccg gcacaagcag gaacattggc gggggaaatg acgtccactg gtaccagcag       120
catccaggga aggcccccaa actgctgatc tccggagtga ttgagcggag ctccggcgtc       180
cccgatagat tcagcgggtc caagtctgga aacacagctt ctctgactat cagtggcctg       240
caggcagagg acgaagccga ttactattgc cagtctttcg acggcagtct gtcagggagc       300
gtgtttggca ctgggaccga tgtgaccgtc ctg                                    333

<210> SEQ ID NO 4
<211> LENGTH: 111
<212> TYPE: PRT
<213> ORGANISM: Artificial Sequence
<220> FEATURE:
<223> OTHER INFORMATION: Amino acid sequence for light chain variable
      region of monoclonal antibody MAB1

<400> SEQUENCE: 4

Gln Ser Glu Leu Thr Gln Pro Arg Ser Val Ser Gly Ser Pro Gly Gln
1               5                   10                  15

Ser Val Thr Ile Ser Cys Thr Gly Thr Ser Arg Asn Ile Gly Gly Gly
            20                  25                  30

Asn Asp Val His Trp Tyr Gln Gln His Pro Gly Lys Ala Pro Lys Leu
        35                  40                  45

Leu Ile Ser Gly Val Ile Glu Arg Ser Ser Gly Val Pro Asp Arg Phe
    50                  55                  60
```

```
Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gln Ser Phe Asp Gly Ser
                 85                  90                  95

Leu Ser Gly Ser Val Phe Gly Thr Gly Thr Asp Val Thr Val Leu
            100                 105                 110

<210> SEQ ID NO 5
<211> LENGTH: 8
<212> TYPE: PRT
<213> ORGANISM: Artificial Sequence
<220> FEATURE:
<223> OTHER INFORMATION: HCDR1

<400> SEQUENCE: 5

Gly Phe Thr Phe Ser Ser Tyr Ser
1               5

<210> SEQ ID NO 6
<211> LENGTH: 8
<212> TYPE: PRT
<213> ORGANISM: Artificial Sequence
<220> FEATURE:
<223> OTHER INFORMATION: HCDR2

<400> SEQUENCE: 6

Ile Ser Ser Ser Ser Ser Tyr Ile
1               5

<210> SEQ ID NO 7
<211> LENGTH: 14
<212> TYPE: PRT
<213> ORGANISM: Artificial Sequence
<220> FEATURE:
<223> OTHER INFORMATION: HCDR3

<400> SEQUENCE: 7

Glu Tyr Asp Phe Trp Ser Ala Tyr Tyr Asp Ala Phe Asp Val
1               5                   10

<210> SEQ ID NO 8
<211> LENGTH: 9
<212> TYPE: PRT
<213> ORGANISM: Artificial Sequence
<220> FEATURE:
<223> OTHER INFORMATION: LCDR1

<400> SEQUENCE: 8

Ser Arg Asn Ile Gly Gly Gly Asn Asp
1               5

<210> SEQ ID NO 9
<211> LENGTH: 3
<212> TYPE: PRT
<213> ORGANISM: Artificial Sequence
<220> FEATURE:
<223> OTHER INFORMATION: LCDR2

<400> SEQUENCE: 9

Gly Val Ile
1

<210> SEQ ID NO 10
<211> LENGTH: 11
<212> TYPE: PRT
```

```
<213> ORGANISM: Artificial Sequence
<220> FEATURE:
<223> OTHER INFORMATION: LCDR3

<400> SEQUENCE: 10

Gln Ser Phe Asp Gly Ser Leu Ser Gly Ser Val
1               5                   10
```